(12) United States Patent
Lanza et al.

(10) Patent No.: US 7,803,374 B2
(45) Date of Patent: Sep. 28, 2010

(54) TARGETED ATHEROSCLEROSIS TREATMENT

(75) Inventors: Gregory M. Lanza, St. Louis, MO (US); Samuel A. Wickline, St. Louis, MO (US)

(73) Assignee: Barnes-Jewish Hospital, St. Louis, MO (US)

( * ) Notice: Subject to any disclaimer, the term of this patent is extended or adjusted under 35 U.S.C. 154(b) by 246 days.

(21) Appl. No.: 10/492,749

(22) PCT Filed: Jan. 16, 2004

(86) PCT No.: PCT/JP2004/001106

§ 371 (c)(1),
(2), (4) Date: Aug. 30, 2006

(87) PCT Pub. No.: WO2005/077407

PCT Pub. Date: Aug. 25, 2005

(65) Prior Publication Data

US 2007/0010577 A1   Jan. 11, 2007

(51) Int. Cl.
*A61K 39/395* (2006.01)
*A61K 39/00* (2006.01)
*A61K 38/00* (2006.01)

(52) U.S. Cl. .................. 424/143.1; 424/184.1; 514/2
(58) Field of Classification Search .............. None
See application file for complete search history.

(56) References Cited

U.S. PATENT DOCUMENTS

| 5,690,907 | A | 11/1997 | Lanza et al. | 424/9.5 |
| 5,780,010 | A | 7/1998 | Lanza et al. | 424/9.32 |
| 5,958,371 | A | 9/1999 | Lanza et al. | 424/1.21 |
| 5,989,520 | A | 11/1999 | Lanza et al. | 424/9.32 |
| 2004/0018228 | A1 | 1/2004 | Fischell et al. | |

FOREIGN PATENT DOCUMENTS

| JP | 2003-514768 | 4/2003 |
| WO | WO-01/17508 | 3/2001 |
| WO | WO-03/047633 | 6/2003 |
| WO | WO-03/062198 | 7/2003 |

OTHER PUBLICATIONS

Anderson et al., Magn. Reson Med. (2000) 44(3):433-439.
International Search Report for PCT/USO4/01106, mailed on Mar. 1, 2005, 3 pages.
Janssen et al., Cancer Res. (2002) 62(21):6146-6151.
Lanza et al., Circulation (2002) 106(22):2842-2847.
Sin et al., Proc. Natl. Acad. Sci. USA (1997) 94(12):6099-60103.
Crowder et al., Journal of the American College of Cardiology (2003) 41(6, Suppl. A):59A.
Goodman et al, Journal of Medicinal Chemistry (2002) 45(31):1045-1051.
Supplementary European Search Report for EP 04702943.4, mailed May 10, 2007, 4 pages.
Winter et al., Circulation (2002) 106(19 Suppl):II-151.
Brooks et al. (1994) *Cell* 79:1157-1164.
Herbst et al. (2002) *J. Clin. Oncol.* 20:4440-4447.
Moulton et al. (1999) *Circulation* 99:1726-1732.
Moulton (2002) *Cold Spring Harb. Symp. Quant. Biol.* 67:471-482.
O'Brien et al. (1994) *Am. J. Pathol.* 145:883-894.
Tenaglia et al. (1998) *Am. Heart J.* 135:10-14.
Wilson et al. (2002) *Circulation* 105:415-418;.
Winter et al. (2003) *Circulation* 108:2270-2274.
Zhang et al. (1993) *Am. J. Pathol.* 143:164-172.
International Preliminary Report on Patentability for PCT/USO4/01106, mailed on Jul. 25, 2006, 5 pages.
Science Blog, Non-invasive imaging technique detects plaques beginning to form in vessels, Nov. 2002, pp. 1-3.
Moulton et al., PNAS USA 100(8):4736-4741.
Notice of Reasons for Rejection (Translation) for JP 2006-549216, mailed Feb. 22, 2010, 10 pages.
Sukhova et al., Arterioscler Thromb Vasc Biol. (2002) 22:1452-1458.

*Primary Examiner*—Maher M Haddad
(74) *Attorney, Agent, or Firm*—Morrison & Foerster LLP

(57) ABSTRACT

This invention relates generally to methods for ameliorating at least one symptom or aspect of atherosclerosis. The methods include administration of targeted carrier compositions comprising a therapeutic agent effective in ameliorating at least one aspect of atherosclerosis coupled to a targeting ligand effective is targeting the therapeutic agent to tissue associated with atherosclerotic plaque.

6 Claims, 4 Drawing Sheets

TARGETED ATHEROSCLEROSIS TREATMENT

CROSS-REFERENCE TO RELATED APPLICATION

This application is a national phase filing of PCT/US04/01106, filed Jan. 16, 2004, the entire content of which is hereby incorporated herein by reference.

TECHNICAL FIELD

This invention relates to methods for treating atherosclerosis, in particular, methods for treating atherosclerotic plaque in primary and secondary preventative strategies. It particularly relates to targeted carrier compositions comprising a therapeutic agent effective in ameliorating at least one aspect of atherosclerosis and comprising a targeting ligand effective is targeting the agent to atherosclerotic plaque.

BACKGROUND OF THE INVENTION

The preponderance of annual mortality in the Western world is caused by atherosclerosis, which often presents as cerebrovascular accident or myocardial infarction. Unfortunately, comprehensive evaluation of atherosclerosis generally ensues only after a clinical event is caused by plaque rupture in the later stages of this disease process.

The close association of angiogenesis with atherosclerosis disease is recognized. See, for example, O'Brien et al. (1994) *Am. J. Pathol.* 145:883-894. Angiogenesis is a critical feature of plaque development in atherosclerosis and may play a key role in both the initiation of plaque development and the later rupture of plaques leading to myocardial infarction and stroke. In atherosclerotic disease, angiogenic vessels primarily develop from the vasa vasorum in the adventitial layer of the plaque and extend into the thickening intimal layer of the atheroma rather than originating from the primary arterial lumen. Extensive neovascular proliferation has been spatially localized to atherosclerotic plaque, and in particular, to "culprit" lesions clinically associated with unstable angina, myocardial infarction and stroke. Plaque angiogenesis appears to play a role in promotion of plaque growth, intraplaque hemorrhage, and lesion instability. See, for example, Zhang et al. (1993) *Am. J. Pathol.* 143:164-172; Tenaglia et al. (1998) *Am. Heart J.* 135:10-14; Moulton (2002) *Cold Spring Harb. Symp. Quant. Biol.* 67:471-482.

Paramagnetic nanoparticles targeted to $\alpha_v\beta_3$-integrins, an angiogenic biomarker expressed by proliferating neovasculature, can provide sensitive and specific detection and characterization of early atherosclerosis in hypercholesterolemic rabbits. See, for example, Winter et al. (2003) *Circulation* 108:2270-2274; Brooks et al. (1994) *Cell.* 79:1157-1164. Such imaging data reaffirmed the diffuse nature of the early atherosclerotic process and illustrated the considerable heterogeneity of disease found within individual aortic segments.

When administered chronically at high dosages, anti-angiogenic agents, such as endostatin and TNP-470, a water soluble form of fumagillin, have shown some activity for decreasing neovascular proliferation and plaque growth in animal models of early atherosclerosis (Wilson et al. (2002) *Circulation* 105:415-418; Moulton et al. (1999) *Circulation* 99:1726-1732). For example, Apo E$^{-/-}$ mice treated for 4 months (20 to 36 weeks) with TNP-470 or endostatin had reduced number of intimal vessels and diminished atheroma expansion despite elevated total cholesterol levels. Neither endostatin nor TNP-470 altered foam cell deposition or fibromuscular lesion development during early atherogenesis, and they were both less effective during later periods of treatment (32 to 48 weeks) (Moulton et al. (1999) Supra). Unfortunately, high dose TNP-470 has serious side effects such as neurocognitive toxicity (Herbst et al. (2002) *J. Clin. Oncol.* 20:4440-4447.

There is a continuing need for the development of methods and compositions that are effective in specifically reaching and reducing unwanted neovasculature, including that associated with atherosclerosis.

All publications and patent applications cited herein are hereby incorporated by reference in their entirety.

BRIEF SUMMARY OF THE INVENTION

The invention is directed to methods and compositions for ameliorating symptoms and disease associated with atherosclerotic plaque.

In some embodiments, the invention is directed to methods for reducing angiogenesis in expanded vasa vasorum tissue in a subject. In another embodiment, the invention is directed to methods for reducing early atherosclerotic plaque burden in a subject. In another embodiment, the invention is directed to methods for atherosclerotic plaque stabilization in a subject. In another embodiment, the invention is directed to methods for atherosclerotic plaque regression in a subject in need thereof.

In one embodiment, compositions for use in the methods of the invention comprise a targeted carrier comprising a targeting ligand specific for vasa vasorum tissue coupled to a therapeutic agent. In some embodiments, the targeted carrier is an emulsion of nanoparticles. In some embodiments, the therapeutic agent is an anti-angiogenic agent.

BRIEF DESCRIPTION OF THE DRAWINGS

FIG. 6a shows an abdominal aorta section (4x) stained for $\alpha_v\beta_3$- integrin expression from an animal treated with $\alpha_v\beta_3$-targeted nanoparticles without fumagillin and reveals a large atherosclerotic plaque. FIG. 6b shows high neovascular expansion of the vasa vasorum expressing $\alpha_v\beta_3$-integrin (black arrows) to support plaque growth in a higher magnification image (60×). FIG. 6c shows an abdominal aorta section (4×) 7 days following $\alpha_v\beta_3$-targeted fumagillin nanoparticle treatment stained for $\alpha_v\beta_3$-integrin expression. FIG. 6d shows absence of angiogenic vessels below residual plaque (red arrows).

DETAILED DESCRIPTION OF THE INVENTION

Figure 1:
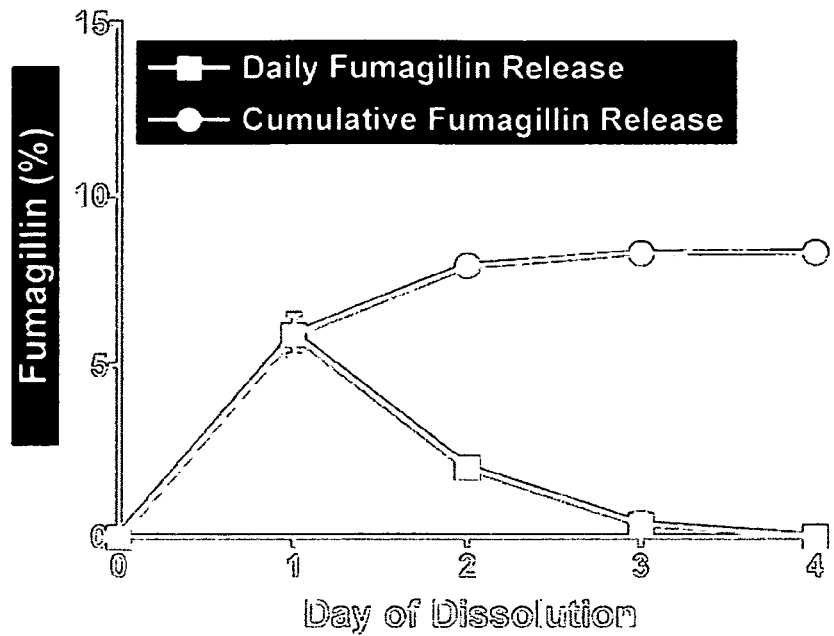
FIG. 1 is a graph which depicts daily (squares) and cumulative (circles) release of fumagillin from nanoparticles.

We have discovered that targeting an anti-angiogenic agent to an expanded vasa vasorum decreases the neovasculature of an atherosclerotic plaque. Targeting such agents in the form of targeted carriers to an expanded vasa vasorum also results in a reduction of early plaque burden in a hyperlipidemic animal. Pathologic roles for plaque neovascularization include: 1) expanding plaques beyond a wall thickness that limits diffusion, 2) conducting inflammatory cells into lesions and 3) instigating plaque instability and rupture. The invention thus provides methods and compositions for use in reducing angiogenesis in expanded vasa vasorum and for reducing early atherosclerotic plaque burden. The invention also provides methods and compositions for use in stabilizing and/or reversing the progression of an atherosclerotic plaque and atherosclerosis disease. Thus, the invention provides methods for treating atherosclerotic plaque in primary (i.e., before clinical presentation) and secondary (i.e., after clinical presentation) preventative strategies. The methods and compositions of the invention can be used early in atherosclerosis, for example, when a plaque is still developing, and/or later in atherosclerosis, for example, to stabilize a formed plaque or after angioplasty, for example, to reduce restenosis.

Targeted carriers for use in the methods of the invention are modified to incorporate at least one therapeutic agent including, but not limited to, agents with cidal activity, anti-angiogenic agents, enzyme inhibitors, metabolic pathway disruptors, apoptotic agents, cytotoxins and anti-inflammatory agents. The therapeutic agent may be on or attached at the surface of the targeted carriers, e.g., particles or within the core of the targeted carrier, e.g., particles.

The targeted carriers are further modified to include a targeting or homing ligand to direct the therapeutic agent to a desired target cell and/or tissue, such as, expanded vasa vasorum and areas of restenosis.

In some embodiments, in addition to delivery of the therapeutic agent, targeted carriers, such as nanoparticles, may be also serve as contrast agents and their delivery to the target can be detected using imaging techniques. Such targeted carriers would permit, for example, the target site to be imaged in order to monitor the progress of the therapy at the site and to make desired adjustments in dosage or therapeutic agent subsequently directed to the site.

The invention provides methods of using the targeted carriers in a variety of applications, including in vivo applications. The invention also provides kits and methods of making the targeted carriers for use in methods of the invention.

Methods of Targeted Atherosclerosis Therapy

The invention provides methods for reducing angiogenesis in expanded vasa vasorum and for reducing early atherosclerotic plaque burden in a subject in need thereof The invention also provides methods for atherosclerotic plaque regression and for atherosclerotic plaque stabilization in a subject in need thereof. The methods comprise administering a targeted carrier composition comprising a targeting ligand and a therapeutic agent for reducing angiogenesis at the target site. The methods are thus of use in ameliorating symptoms associated with vascular and/or restenosis pathology. Injury to the vascular wall can occur with ballon-overstretch during an angioplasty procedure.

The targeted carrier compositions of the invention comprise a targeting ligand to direct the carrier complex primarily to an expanded vasa vasorum so that the anti-angiogenic agent is delivered to the site at which it is most effective. For example, nanoparticles containing a ligand that binds to $\alpha_v\beta_3$ integrin are targeted to tissues containing high expression levels of $\alpha_v\beta_3$ integrin, such as vasa vasorum. High expression levels of $\alpha_v\beta_3$ are typical of activated endothelial cells and are considered diagnostic for neovasculature. The methods allow for administration of a reduced amount of anti-angiogenic agent as compared to that delivered without targeting.

As demonstrated herein, administration of nanoparticles containing anti-angiogenic agent (fumagillin) with a targeting ligand directed to targets containing high levels of $\alpha_v\beta_3$ integrin results in enhanced delivery of the agent to expanded vasa vasorum as compared to agent delivery with a non-targeted particle containing the agent and as compared to administration of the agent alone. Use of the targeted nanoparticles to deliver the fumagillin allowed for a $5.6\times10^4$ fold lower amount of the drug to be administered as compared to the amount of TNP-470 administered in Moulton et al. (1999) Supra. Moulton et al. (1999) report administration of 30 mg TNP-470 per kg every other day for 13 weeks, or a total of 1.67 g/kg. As presented herein, the amount of fumagillin administered one time in the targeted nanoparticles was 30 µg/kg. Being able to reduce the amount of therapeutic agent delivered may be clinically relevant since agents can often have significant side effects. See, for example, Herbst et al. (2002), Supra.

The use of the targeted carriers containing a therapeutic agent also provides for delivery of imaging agents to the target site such as lanthanides (e.g., gadolinium), radionuclides, iron oxides, optically active agents (e.g., fluorophores), or x-ray contrast agents (e.g., iodine), among others. Generally, the nanoparticles described herein are inherently acoustically reflective as well. Thus, in some embodiments, targeted cells can be identified, agent delivery to the cell can be confirmed and/or effect of the targeted agent can be monitored using known imaging techniques and while employing conventional imaging equipment. Being able to quantify the local drug concentration can allow more monitoring and control over the amount of drug administered. In addition to combining therapeutic agent delivery with imaging, targeted carriers of the invention can be used in single-modal or multi-modal imaging. For example, multi-modal imaging can be performed with targeted carriers including ancillary reagents that allow for more than one type of imaging.

The invention thus provides a noninvasive means for the therapeutic treatment of nascent or developing plaques, atherosclerotic plaques, plaque formation associated with restenosis, an over-robust healing response associated with restenosis, infarction, atherosclerosis and inflammatory conditions, for example, in patients. Generally, anti-angiogenic agents are delivered to expanded vasa vasorum associated with the neovasculature or plaque in cardiovascular-related tissues, including, but limited to, heart tissue and all cardiovascular vessels, angiogenic tissue, any part of a cardiovascular vessel and the like. Disease conditions to be treated using the methods of the invention include, but are not limited to, any disease condition in which vasculature plays an important part in pathology, for example, cardiovascular disease, cancer, areas of inflammation, which may characterize a variety of disorders including rheumatoid arthritis, areas of irritation such as those affected by angioplasty resulting in restenosis, tumors, and areas affected by atherosclerosis. Other tissues of interest to be treated include those containing particular malignant tissue and/or tumors, and tissues exhibiting inflammatory responses such as arthritis, vasculitis, or autoimmune diseases.

Since most prospective patients will present underlying atherosclerosis and associated vasa vasorum expansion, the clinical decision to initiate a primary preventive strategy will likely depend on a combination of known risk factors and a quantitative excess risk estimate of early atherosclerotic disease burden. Since this disease process is heterogeneously distributed within the vasculature, regional severity will need to be elucidated as well as the overall burden. Follow-up monitoring will require the same quantitative, segmental precision.

The targeted carriers and targeted carrier compositions described herein are useful in the methods of the invention and can be used with cells or tissues in vivo, ex vivo, in situ and in vitro.

Methods of administering the targeted carriers of the invention are well known to those in the art. The targeted carriers of the present invention are administered, for example, by intravenous injection. In some instances, nanoparticulate targeted carriers are administered by infusion at a rate of approximately 1-3 ml/minute. In some embodiments, the targeted carriers may be administered locally by, for example, catheter instillation at a particular site. Although the targeted carriers are typically administered to the vasculature, after administration, targeted carriers may go outside of the vasculature and reach additional cells and/or tissue.

The effective amount and method of administration of the particular targeted carrier formulation can vary based on the individual, desired result and/or type of disorder, the stage of the disease and other factors evident to one skilled in the art. The route(s) of administration useful in a particular application are apparent to one of skill in the art.

The targeted carrier compositions of the invention are administered as pharmaceutically acceptable compositions. The compositions may be administered by any suitable means, including, but not limited to, intravenously, parenterally or locally. The compositions can be administered in a single dose by bolus injection or continuous infusion or in several doses over selected time intervals in order to titrate the dose.

For methods for secondary preventative strategies, the targeted carrier composition may be administered at the time of injury, e.g., immediately after an angioplasty procedure, and/ or at a time following the injury or after beginning of restenosis. For example, the targeted carrier composition may be administered about one hour, about 12 hours, about 1 day, about 3 days, about 7 days, about 2 weeks, about 3 weeks, up to about 4 weeks after an angioplasty procedure. The compositions may be administered one or more, two or more or three or more times, as needed.

As used herein, an "individual" or "subject" is a vertebrate, preferably a mammal, more preferably a human. Mammals include, but are not limited to, humans, farm animals, sport animals, rodents and pets.

As used herein, an "effective amount" or a "sufficient amount" of a substance is that amount sufficient to effect beneficial or desired results, including clinical results, and, as such, an "effective amount" depends upon the context in which it is being applied. An effective amount can be administered in one or more administrations.

As used herein, the singular form "a", "an", and "the" includes plural references unless indicated otherwise. For example, "a" target cell includes one or more target cells.

If imaging is performed in conjunction with the therapeutic delivery, known techniques can be used, such as for example, magnetic resonance imaging (MRI), nuclear, optical, CT, or positron emission tomography (PET) methods if appropriate formulations are produced in concert with the therapeutic delivery. For methods in which MRI is performed, nanoparticulate emulsions with contrast agents may be used in a similar manner as other MRI agents as described in U.S. Pat. Nos. 5,155,215 and 5,087,440; Margerstadt et al. (1986) *Magn. Reson. Med.* 3:808; Runge et al (1988) *Radiology* 166:835; and Bousquet et al. (1988) *Radiology* 166:693. Other agents that may be employed are those set forth in U.S. Pat. publication 2002/0127182 which are pH sensitive and can change the contrast properties dependent on pulse. Generally, sterile aqueous solutions of the contrast agents are administered to a patient intravenously in dosages ranging from 0.01 to 1.0 mmoles per kg body weight.

If used, diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures. In embodiments in which therapeutic radiopharmaceuticals are administered, the therapeutic radiopharmaceutical is administered, for example, by intravenous injection, usually in saline solution, at a dose of 0.01 to 5 mCi per kg body weight, or preferably at a dose of 0.1 to 4 mCi per kg body weight. These dosages are higher than corresponding imaging isotopes.

For X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

For ultrasound contrast agents, the compositions are generally administered by intravenous injection. For example, lipid microbubbles are administered in an amount of 10 to 30 µL of the echogenic gas per kg body weight or by infusion at a rate of approximately 10 µg/min. Imaging is performed using known techniques of sonography.

Compositions of the Invention

A targeted carrier for use in the present invention refers to a targeting ligand coupled to a therapeutic agent. As used herein, entities that are "coupled" are associated, joined, linked attached or connected either directly or indirectly. For example, in some embodiments, the targeting ligand and the therapeutic agent of the targeted carrier may be coupled through co-localization in and/or on a particle, liposome, emulsion, hydrogel, niosome and the like, so that both entities are co-directed to the target cell or tissue. In other embodiments, the targeting ligand and the therapeutic agent of the targeted carrier may be directly coupled in a complex through covalent and/or noncovalent association. In other embodiments, the targeting ligand and the therapeutic agent of the targeted carrier may be indirectly coupled through at least one intermediate component by covalent and/or noncovalent association.

As used herein, a "therapeutic agent" refers to an agent which stabilizes disease activity when delivered to regions containing expanded vasa vasorum and/or atherosclerotic plaques. Such therapeutic agents include, but are not limited to, agents with cidal activity, anti-angiogenic agents, enzyme inhibitors, metabolic pathway disruptors, and anti-inflammatory agents.

In some embodiments, the therapeutic agents are incorporated within or on the surface of the targeted carriers. In some embodiments, the therapeutic agents are incorporated within the core of the targeted carriers. As described herein, the targeted carrier compositions of the invention incorporate therapeutic agents (e.g. drugs, prodrugs, genetic materials, radioactive isotopes, or combinations thereof) in their native form or derivatized with hydrophobic or charged moieties to enhance incorporation or adsorption onto or into the targeted carrier complex. In some embodiments, the therapeutic agents can be derivatized with a lipid anchor to make the agent lipid soluble or to increase its solubility in lipid, therefore increasing retention of the agent in the lipid layer of the emulsion and/or in the lipid membrane of the target cell. The therapeutic agent may be a prodrug, including prodrug formulations as described, for example, by Sinkyla et al. (1975) J. Pharm. Sci. 64:181-210, Koning et al. (1999) Br. J. Cancer 80:1718-1725, U.S. Pat. No. 6,090,800 and U.S. Pat. No. 6,028,066.

Anti-angiogenic agents contemplated for use in the invention include those that act through inhibiting matrix breakdown, inhibiting endothelial cell replication and/or activity, and/or through inhibiting molecules which activate angiogenesis. In some instances, anti-angiogenic agents which inhibit the activity of activated endothelial cells are of particular interest. Accordingly, anti-angiogenesis agents for use in the invention include, but are not limited to, matrix metalloproteinase (MMPs) inhibitors (e.g., inhibitors of MMP-2, MMP-9), tissue inhibitor of metalloproteinases (TIMPs, e.g., TIMP-1, TIMP-2, TIMP-3), marimistat, neovastat, thrombospondin-1, internal fragments of thrombospondin-1, METH-1 and METH-2 (proteins containing metalloprotease and thrombospondin domains and disintegrin domains in amino termini), fumagillin, fumagillin analogue TNP-470, endostatin, simvastatin, vasculostatin, vasostatin, angiostatin, protein kinase C beta inhibitor, genistein, anti-integrins, vascular endothelial growth factor inhibitor (VEGF-inhibitor), fragment of platelet factor-4 (amino-terminal fragment), derivative of prolactin, restin, angiopoietin-2 (antagonist of angiopoietin-1), proliferin-related protein, heparinase, anti-thrombin III fragment (fragment missing the carboxy-terminal loop of antithrombin H), bFGF-binding molecules, bFGF inhibitors, prolactin 16-kD fragment (derivative of prolactin), SPARC cleavage product, osteospontin cleavage product, thalidomide, squalamine, interferons (e.g., interferon-alpha, interferon-beta), interferon-inducible protein-10, anthracycline, 15-deoxyspergualin, D-penicillamine, eponemycin, herbimycin A, and rapamycin. Agents which may also inhibit VEGF activity include VEGF-neutralizing chimeric proteins such as soluble VEGF receptors and may be VEGF-receptor-IgG chimeric proteins. bFGF inhibitors may include bFGF-neutralizing chimeric proteins such as soluble bFGF receptors and may be bFGF-receptor-IgG chimeric proteins.

In some embodiments, therapeutic agents include radionuclides, including alpha emitters (e.g., $^{225}$Ac) and beta emitters (e.g., $^{90}$Y).

Therapeutic agents of use in the invention include agents which inhibit the activity of proangiogenic growth factors. Proangiogenic growth factor inhibitors may be in the form of antagonists which block or prevent effective production of a proangiogenic growth factor, antagonists which block or prevent effective binding of a proangiogenic growth factor to its receptor, and/or antagonists which block or prevent effective signaling of a proangiogenic growth factor. Agents with such inhibitor activity can be of a wide variety, including proteins (e.g., antibodies or antibody fragments), nucleic acids (e.g., antisense molecules, expression vectors encoding inhibitor), pharmaceuticals and the like. Examples of proangiogenic growth factors include vascular endothelial growth factor (VEGF), basic fibroblast growth factor (bFGF), acidic fibroblast growth factor (aFGF), fibroblast growth factor-3, fibroblast growth factor4, transforming growth factor-alpha (TGF-alpha), epidermal growth factor (EGF), hepatocyte growth factor/scatter factor (HGF/SF), tumor necrosis factor-alpha (TNF-alpha), placental growth factor, platelet-derived growth factor (PDGF), granulocyte colony-stimulating factor, pleiotropin, interleukin-8, thymidine phosphorylase (TP)-platelet-derived endothelial cell growth factor (PD-ECGF), angiogenin and proliferin.

Genetic material of use as a therapeutic agent in the invention includes that which blocks formation and/or development of vasa vasorum neovasculature or neovasculature associated with restenosis, for example, genetic material which leads to inhibition of angiogenesis (e.g., which blocks activity of proangiogenic factors) or which leads to cidal activity or death in cells responsible for angiogenesis (e.g., endothelial cells). Therapeutic agents in the form of genetic material, include, for example, nucleic acids, RNA and DNA, of either natural or synthetic origin, including recombinant RNA and DNA and antisense RNA and DNA; hammerhead RNA, ribozymes, hammerhead ribozymes, antigene nucleic acids, both single and double stranded RNA and DNA and analogs thereof, immunostimulatory nucleic acid, ribooligonucleotides, antisense ribooligonucleotides, deoxyribooligonucleotides, and antisense deoxyribooligonucleotides. Other types of genetic material that may be used include, for example, genes carried on expression vectors such as plasmids, phagemids, cosmids, yeast artificial chromosomes, and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers.

The term "ligand" as used herein is intended to refer to a targeting molecule that binds specifically to another molecule of a biological target separate and distinct from the targeted carrier complex itself. The reaction does not require nor exclude a molecule that donates or accepts a pair of electrons to form a coordinate covalent bond with a metal atom of a coordination complex. Thus, in some embodiments, a ligand may be attached covalently for direct-conjugation or noncovalently for indirect conjugation to the surface of the particle or carrier surface.

The targeting ligand coupled to the surface of the targeted carrier is generally specific for a desired target to allow active targeting. Active targeting refers to ligand-directed, site-specific accumulation of agents to cells, tissues or organs by localization and binding to molecular epitopes, e.g., receptors, lipids, peptides, cell adhesion molecules, polysaccharides, biopolymers, and the like, presented on the surface membranes of cells or within the extracellular or intracellular matrix. A wide variety of ligands can be used including an antibody, a fragment of an antibody, a polypeptide such as small oligopeptide, a large polypeptide or a protein having three dimensional structure, a peptidomimetic, a polysaccharide, an aptamer, a lipid, a nucleic acid, a lectin or a combination thereof. Generally, the ligand specifically binds to a cellular epitope or receptor.

The targeted carriers of the present invention employ targeting ligands for molecules expressed on or in neovasculature, in particular, neovasculature of the vasa vasorum. The targeting ligand serves to increase the concentration of the targeted carrier, and thus therapeutic agent, at a site of angiogenic activity. Neovascular components of the vasa vasorum include activated or proliferating endothelial cells. Thus, targeting ligand for use in the targeted carriers include those that specifically or preferentially direct the complexes, e.g., nanoparticles, to activated or proliferating endothelial cells in the vasa vasorum. For example, $\alpha_v\beta_3$-integrin is expressed on angiogenic vasculature and ligands specific for the $\alpha_v\beta_3$-integrin are of use as targeting ligands in the present invention.

Further description of the various kinds of targeting ligands and methods of formulating targeted carriers with targeting ligands is provided herein, in particular, later in this Compositions section.

In addition to the targeting ligand and therapeutic agent, the targeted carriers may contain associated with their surface an "ancillary agent" useful in imaging and/or therapy with a radionuclide, a contrast agent for magnetic resonance imaging (MRI) or for X-ray imaging or a fluorophore. The targeted carrier complexes themselves, in some instances, e.g., nanoparticulate emulsion, can serve as contrast agents for ultrasound imaging.

In the embodiments where the targeted carrier complex is in the form of a nanoparticle, any nanoparticulate emulsion may be used in the methods and compositions of the invention. For example, PCT publication W095/03829 describes oil emulsions where the drug is dispersed or solubilized inside an oil droplet and the oil droplet is targeted to a specific location by means of a ligand. U.S. Pat. No. 5,542,935 describes site-specific drug delivery using gas-filled perfluorocarbon microspheres. The drug delivery is accomplished by permitting the microspheres to home to the target and then effecting their rupture. Low boiling perfluoro compounds are used to form the particles so that the gas bubbles can form.

In some instances, however, emulsions are preferred in which the nanoparticles are based on high boiling perfluorocarbon liquids such as those described in U.S. Pat. No. 5,958, 371. The liquid emulsion contains nanoparticles comprised of relatively high boiling perfluorocarbons surrounded by a coating which is composed of a lipid and/or surfactant. The surrounding coating is able to couple directly to a targeting ligand or can entrap an intermediate component which is covalently coupled to the targeting ligand, optionally through a linker, or may contain a non-specific coupling agent such as biotin. Alternatively, the coating may be cationic so that negatively charged targeting ligands such as nucleic acids, in general, or aptamers, in particular, can be adsorbed to the surface. The surface and/or core of the nanoparticulate emulsion also contains at least one therapeutic agent, e.g., an anti-angiogenic agent, for delivery to the targeted cells or tissue.

In some embodiments, the emulsion for administration is a nanoparticulate system containing a high boiling perfluorocarbon as a core and an outer coating that is a lipid/surfactant mixture which provides a vehicle for binding a multiplicity of copies of one or more desired components to the nanoparticle. The nanoparticle emulsion and formulation for use in the methods of the invention, the construction of the basic particles and the formation of emulsions containing them, regardless of the components bound to the outer surface is described in U.S. Pat. Nos. 5,690,907, 5,780,010, 5,989,520 and 5,958,371, all of which are incorporated herein by reference.

Typically, the nanoparticle emulsions are comprised of at least two immiscible liquids which are intimately dispersed, preferably, a hydrophobic material such as an oil, dispersed in water. The emulsions are in the form of droplets or nanoparticles having a diameter which typically is about 0.2 µm. Additives such as surface-active agents or finely-divided solids can be incorporated into the emulsion nanoparticles to increase their stability. The nanoparticles typically have a lipid monolayer bounding the hydrophobic core.

Fluorocarbon emulsions and, in particular, perfluorocarbon emulsions are well suited for biomedical applications and for use in the practice of the present invention. The perfluorocarbon emulsions are known to be stable, biologically inert and readily metabolized, primarily by trans-pulmonic alveolae evaporation. Further, their small particle size easily accommodates transpulmonic passage and their circulatory half-life ("beta elimination" half time: 1-2 hours) advantageously exceeds that of other agents. Also, perfluorocarbons have been used to date in a wide variety of biomedical applications, including use as artificial blood substitutes. For use in the present invention, various fluorocarbon emulsions may be employed including those in which the fluorocarbon is a fluorocarbon-hydrocarbon, a perfluoroalkylated ether, polyether or crown ether. Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorotributylamine, perfluorodecalin, perfluorooctylbromide, perfluorodichlorooctane, perfluorodecane, perfluorotripropylamine, perfluorotrimethylcyclohexane or other perfluorocarbon compounds. Further, mixtures of such perfluorocarbon compounds may be incorporated in the emulsions utilized in the practice of the invention.

Emulsifying agents, for example surfactants, are used to facilitate the formation of emulsions and increase their stability. Typically, aqueous phase surfactants have been used to facilitate the formation of oil-in-water emulsions. A surfactant is any substance that contains both hydrophilic and a hydrophobic portions. When added to water or solvents, a surfactant reduces the surface tension.

The oil phase of the oil-in-water emulsion comprises, for example, 5 to 50% and, in some instances, 20 to 40% by weight of the emulsion. In some embodiments, the oil phase may comprise fatty acid esters such as triacylglycerol (corn oil). In some embodiments, the oil or hydrophobic constituent is a fluorochemical liquid. The fluorochemical liquid includes straight, branched chain and cyclic perfluorocarbons, straight, branched chain and cyclic perfluoro tertiary amines, straight, branched chain and cyclic perfluoro ethers and thioethers, chlorofluorocarbons and polymeric perfluoro ethers and the like. Although up to 50% hydrogen-substituted compounds can be used, perhalo compounds are preferred. Most preferred are perfluorinated compounds. Any fluorochemical liquid, i.e. a substance which is a liquid at or above body temperature (e.g. 37° C.) at atmospheric pressure, can be used to prepare a fluorochemical emulsion of the present invention. However, for many purposes emulsions with fluorochemicals with longer extended stability are preferred. In order to obtain such emulsions, fluorochemical liquids with boiling points above 50° C. can be used, and in some cases, fluorochemical liquids with boiling points above about 80° C. can be used.

In an example, the nanoparticles may be constituted by a perfluorocarbon emulsion, the particles having an outer coating of a derivatized natural or synthetic phospholipid, a fatty acid, cholesterol, lipid, sphingomyelin, tocopherol, glucolipid, sterylamine, cardiolipin, a lipid with ether or ester linked fatty acids or a polymerized lipid.

As a specific example of a perfluorocarbon emulsion useful in the invention, a perfluorodichlorooctane or perfluorooctylbromide emulsion may include a lipid coating thereof which contains between approximately 50 to 99.5 mole percent lecithin, preferably approximately 55 to 70 to mole percent lecithin, 0 to 50 mole percent cholesterol, preferably approximately 25 to 45 mole percent cholesterol and approximately 0.5 to 10 mole percent phosphatidylethanolamine, preferably approximately 1 to 5 mole percent phosphatidylethanolamine.

For embodiments in which a biotinylated emulsion is required, the lipid coating of a perfluorodichlorooctane or perfluorooctylbromide emulsion may contain between approximately 50 to 99.5 mole percent lecithin, preferably approximately 55 to 70 to mole percent lecithin, 0 to 50 mole percent cholesterol, preferably approximately 25 to 45 mole percent cholesterol and approximately 0.5 to 10 mole percent biotinylated phosphatidylethanolamine, preferably approximately 1 to 5 mole percent biotinylated phosphatidylethanolamine. Other phospholipids such as phosphatidylserine may be biotinylated, fatty acyl groups such as stearylamine may be conjugated to biotin, or cholesterol or other fat soluble chemicals may be biotinylated and incorporated in the lipid coating for the particles. The preparation of an exemplary biotinylated perfluorocarbon for use in the practice of the invention is described in accordance with known procedures.

The lipid/surfactants used to form an outer coating on the particles (that can contain the coupled targeting ligand or entrap reagents for binding desired components to the surface) include natural or synthetic phospholipids, fatty acids, cholesterols, lysolipids, sphingomyelins, tocopherols, glucolipids, stearylarnines, cardiolipins, plasmalogens, a lipid with ether or ester linked fatty acids, and polymerized lipids. In some instances, the lipid/surfactant can include lipid conjugated polyethylene glycol (PEG). Various commercial anionic, cationic, and nonionic surfactants can also be employed, including Tweens, Spans, Tritons, and the like. In some embodiments, preferred surfactants are phospholipids and cholesterol.

Fluorinated surfactants which are soluble in the oil to be emulsified can also be used. Suitable fluorochemical surfactants include perfluorinated alkanoic acids such as perfluorohexanoic and perfluorooctanoic acids and amidoamine derivatives. These surfactants are generally used in amounts of 0.01 to 5.0% by weight, and preferably in amounts of 0.1 to 1.0%. Other suitable fluorochemicai surfactants include perfluorinated alcohol phosphate esters and their salts; perfluorinated sulfonamide alcohol phosphate esters and their salts; perfluorinated alkyl sulfonamide; alkylene quaternary ammonium salts; N,N(carboxyl-substituted lower alkyl) perfluorinated alkyl sulfonamides; and mixtures thereof. As used herein, the term "perfluorinated" means that the surfactant contains at least one perfluorinated alkyl group.

Suitable perfluorinated alcohol phosphate esters include the free acids of the diethanolamine salts of mono- and bis (1H, 1H, 2H, 2H-perfluoroalkyl)phosphates. The phosphate salts, available under the tradename ZONYL RP (Dupont, Wilmington, Del.), are converted to the corresponding free acids by known methods. Suitable perfluorinated sulfonamide alcohol phosphate esters are described in U.S. Pat. No. 3,094,547. Suitable perfluorinated sulfonamide alcohol phosphate esters and salts of these include perfluoro-n-octyl-N-ethylsulfonamidoethyl phosphate, bis(perfluoro-n-octyl-N-ethylsulfonamidoethyl) phosphate, the ammonium salt of bis (perfluoro-n-octyl-N-ethylsulfonamidoethyl) phosphate, bis (perfluorodecyl-N-ethylsulfonamidoethyl)-phosphate and bis(perfluorohexyl-N ethylsulfonamidoethyl)phosphate. The preferred formulations use phosphatidylcholine, derivatized-phosphatidylethanolamine and cholesterol as the lipid surfactant.

Other known surfactant additives such as PLURONIC F-68, HAMPOSYL L30 (W.R. Grace Co., Nashua, N.H.), sodium dodecyl sulfate, Aerosol 413 (American Cyanamid Co., Wayne, N.J.), Aerosol 200 (American Cyanamid Co.), LIPOPROTEOL LCO (Rhodia Inc., Manmmoth, N.J.), STANDAPOL SH 135 (Henkel Corp., Teaneck, N.J.), FIZUL 10-127 (Finetex Inc., Elmwood Park, N.J.), and CYCLOPOL SBFA 30 (Cyclo Chemicals Corp., Miami, Fla.); amphoterics, such as those sold with the trade names: DERIPHAT 170 (Henkel Corp.), LONZAINE JS (Lonza, Inc.), NIRNOL C2N-SF (Miranol Chemical Co., Inc., Dayton, N.J.), AMPHOTERGE W2 (Lonza, Inc.), and AMPHOTERGE 2WAS (Lonza, Inc.); non-ionics, such as those sold with the trade names: PLURONIC F-68 (BASF Wyandotte, Wyandotte, Mich.), PLURONIC F-127 (BASF Wyandotte), BRIJ 35 (ICI Americas; Wilmington, Del.), TRITON X-100 (Rohm and Haas Co., Philadelphia, Pa.), BRIJ 52 (ICI Americas), SPAN 20 (ICI Americas), GENEROL 122 ES (Henkel Corp.), TRITON N42 (Rohm and Haas Co.), TRITON N-101 (Rohm and Haas Co.), TRITON X-405 (Rohm and Haas Co.), TWEEN 80 (ICI Americas), TWEEN 85 (ICI Americas), and BRIJ 56 (ICI Americas) and the like, may be used alone or in combination in amounts of 0.10 to 5.0% by weight to assist in stabilizing the emulsions.

Nanoparticles may be formulated with cationic lipids in the surfactant layer that facilitate entrapping or adhering ligands, such as nucleic acids and aptamers, to particle surfaces. Typical cationic lipids may include DOTMA, N-[1-(2,3-dioleoyloxy)propyl]-N,N,N-trimethylammonium chloride; DOTAP, 1,2-dioleoyloxy-3-(trimethylammonio)propane; DOTB, 1,2-dioleoyl-3-(4'-trimethyl-ammonio)butanoyl-sn-glycerol,1, 2-diacyl-3-trimethylammonium-propane; DAP, 1,2-diacyl-3-dimethylammonium-propane; TAP, 1,2-diacyl-3-trimethylammonium-propane; 1,2-diacyl-sn-glycerol-3-ethyl phosphocholine; 3β-[N',N'-dimethylaminoethane)-carbamol]cholesterol-HCl, DC-Cholesterol (DC-Chol); and DDAB, dimethyldioctadecylammonium bromide. In general the molar ratio of cationic lipid to non-cationic lipid in the lipid surfactant monolayer may be, for example, 1:1000 to 2:1, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid component of the surfactant, particularly dipalmitoylphosphatidylcholine, dipalmitoylphosphatidylethanolamine or dioleoylphosphatidylethanolamine in addition to those previously described. In lieu of cationic lipids as described above, lipids bearing cationic polymers such as polylysine or polyarginine may also be included in the lipid surfactant and afford binding of a negatively charged therapeutic, such as genetic material or analogues there of, to the outside of the emulsion particles. In some embodiments, the lipids can be cross-linked to provide stability to the particles for use in vivo.

When the targeted carrier is constituted by a liposome, such a liposome may be prepared as generally described in the literature (see, for example, Kimelberg et al., *CRC Crit. Rev. Toxicol.* 6:25, 1978; Yatvin et al., *Medical Physics* 9:149, 1982; Lasic (1993) "Liposomes: from Physics to Applications" Elsevier, Amsterdam). Liposomes are known to the art and generally comprise lipid materials including lecithin and sterols, egg phosphatidyl choline, egg phosphatidic acid, cholesterol and alpha-tocopherol.

Liposomes are small vesicles composed of an aqueous medium surrounded by lipids arranged in spherical bilayers. Liposomes are usually classified as small unilamellar vesicles (SUV), large unilamellar vesicles (LUV), or multi-lamellar vesicles (LV). SUVs and LUVs, by definition, have only one lipid bilayer, whereas MLVs contain many concentric bilayers. Liposomes may be used to encapsulate various therapeutic agents and materials, by trapping hydrophilic molecules in the aqueous interior or between bilayers, or by trapping hydrophobic molecules within the bilayer.

The composition of the lipid bilayer, forming the structural basis for the liposome is generally composed at least of phospholipids, and more generally of mixtures of phospholipids with lipids per se. For example, in the liposomes, phosphatidylcholine derivatives, phosphatidylglycerol derivatives and the like are used along with non phospholipid components, if desired, such as cholesterol. Suitable alternative embodiments include mixtures of phospholipids with, for example, triglycerides. In addition, fatty acids, lipid vitamins, steroids, lipophilic drugs and other lipophilic compounds that can be included in a stable lipid bilayer which either do or do not include phospholipids can be used. Other lipids for use in liposomes include, for example, diacylglycerols.

In some liposome embodiments, phospholipids are included and the liposomes may carry a net positive charge, a net negative charge or can be neutral. Inclusion of diacetylphosphate is a convenient method for conferring negative charge; stearylamine can be used to provide a positive charge. In some instances, at least one head group of the phospholipids is a phosphocholine, a phosphoethanolamine, a phosphoglycerol, a phosphoserine, or a phosphoinositol.

In some embodiments, the targeted carrier is a lipid micelle or a lipoprotein micelle. Micelles are self-assembling particles composed of amphipathic lipids or polymeric components that are utilized for the delivery of sparingly soluble agents present in the hydrophobic core. Various means for the preparation of micellar delivery vehicles are available and may be carried out with ease by one skilled in the art. For instance, lipid micelles may be prepared as described in Perkins et al. (2000) *Int. J. Pharm.* 200:27-39. Lipoprotein micelles can be prepared from natural or artificial lipoproteins including low and high-density lipoproteins and chylomicrons.

In some embodiments, the targeted carrier is a nanoparticle or microparticle which comprises a polymeric shell (nanocapsule), a polymer matrix (nanosphere) or a block copolymer, which may be cross-linked or else surrounded by a lipid layer or bilayer. Such lipid encapsulated nanoparticles and microparticles further comprise a therapeutic agent within the shell, dispersed throughout the matrix and/or within a hydrophobic core. General methods of preparing such nanoparticles and microparticles are described in the art, for example, in Soppimath et al. (2001) *J. Control Release* 70:1-20 and Allen et al. (2000) *J. Control Release* 63:275-286. For example, polymers such as polycaprolactone and poly(d,l-lactide) may be used while the lipid layer is composed of a mixture of lipid as described herein. Derivatized single chain polymers are polymers adapted for covalent linkage of a biologically active agent to form a polymer-agent conjugate. Numerous polymers have been proposed for synthesis of polymer-agent conjugates including polyaminoacids, polysaccharides such as dextrin or dextran, and synthetic polymers such as N-(2-hydroxypropyl)methacrylamide (HPMA) copolymer. Suitable methods of preparation are described in the art, for example, in Veronese et al. (1999) *IL Farmaco* 54:497-516. Other suitable polymers can be any known in the art of pharmaceuticals and include, but are not limited to, naturally-occurring polymers such as hydroxyethyl starch, proteins, glycopeptides and lipids. The synthetic polymers can also be linear or branched, substituted or unsubstituted, homopolymeric, co-polymers, or block co-polymers of two or more different synthetic monomers.

In some embodiments, the targeted carrier is a non-lipid liposome, such as a niosome. In some embodiments, the targeted carrier is a hydrogel. Various means for the preparation of such carrier complexes are available and may be carried out with ease by one skilled in the art.

In particular embodiments, included in the lipid/surfactant coating are components with reactive groups that can be used to couple the targeting ligand and/or the therapeutic agent and/or an ancillary substance useful for therapy and/or imaging. In some embodiments, a lipid/surfactant coating which provides a vehicle for binding a multiplicity of copies of one or more desired components to the particle is preferred. As will be described below, the lipid/surfactant components can be coupled to these reactive groups through functionalities contained in the lipid/surfactant component. For example, phosphatidylethanolamine may be coupled through its amino group directly to a desired moiety, or may be coupled to a linker such as a short peptide which may provide carboxyl, amino, or sulfhydryl groups as described below. Alternatively, standard linking agents such a maleimides may be used. A variety of methods may be used to associate the targeting ligand, therapeutic agent and the ancillary substances, if any, to the particles; these strategies may include the use of spacer groups such as polyethyleneglycol or peptides, for example.

For example, lipid/surfactant coated nanoparticles are typically formed by microfluidizing a mixture of the oil which forms the core and the lipid/surfactant mixture which forms the outer layer in suspension in aqueous medium to form an emulsion. In this procedure, the lipid/surfactants may already be coupled to additional ligands when they are emulsified into the nanoparticles, or may simply contain reactive groups for subsequent coupling. Alternatively, the components to be included in the lipid/surfactant layer may simply be solubilized in the layer by virtue of the solubility characteristics of the ancillary material. Sonication or other techniques may be required to obtain a suspension of the lipid/surfactant in the aqueous medium. Typically, at least one of the materials in the lipid/surfactant outer layer comprises a linker or functional group which is useful to bind the additional desired component or the component may already be coupled to the material at the time the emulsion is prepared.

The covalent linking of the targeting ligands and/or therapeutic agents to the materials in the lipid-encapsulated particles may be accomplished using synthetic organic techniques which would be readily apparent to one of ordinary skill in the art based on the present disclosure. For example, the targeting ligand and/or therapeutic agent may be linked to the material, including the lipid, via the use of well known coupling or activation agents.

For coupling by covalently binding the targeting ligand and/or therapeutic agent or other organic moiety to the components of the outer layer, various types of bonds and linking agents may be employed. Typical methods for forming such coupling include formation of amides with the use of carbodiamides, or formation of sulfide linkages through the use of unsaturated components such as maleimide. Other coupling agents include, for example, glutaraldehyde, propanedial or butanedial, 2-iminothiolane hydrochloride, bifunctional N-hydroxysuccinimide esters such as disuccinimidyl suberate, disuccinimidyl tartrate, bis[2-(succinimidooxycarbonyloxy)ethyl]sulfone, heterobifunctional reagents such as N-(5-azido-2-nitrobenzoyloxy)succinimide, succinimidyl 4-(N-maleimidomethyl)cyclohexane-1-carboxylate, and succinimidyl 4-(p-maleimidophenyl)butyrate, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. Linkage can also be accomplished by acylation, sulfonation, reductive amination, and the like. A multiplicity of ways to couple, covalently, a desired ligand to one or more components of the outer layer is well known in the art. The ligand itself may be included in the surfactant layer if its properties are suitable. For example, if the ligand and/or therapeutic agent contains a highly lipophilic portion, it may itself be embedded in the lipid/surfactant coating. Further, if the ligand and/or therapeutic agent is capable of direct adsorption to the coating, this too will effect its coupling. For example, nucleic acids, because of their negative charge, adsorb directly to cationic surfactants.

The covalent bonds may involve crosslinking and/or polymerization. Crosslinking generally refers to the attachment of two chains of polymer molecules by bridges, composed of either an element, a group, or a compound, which join certain carbon atoms of the chains by covalent chemical bonds. For example, crosslinking may occur in polypeptides which are joined by the disulfide bonds of the cystine residue. Crosslinking may be achieved, for example, by (1) adding a chemical substance (cross-linking agent) and exposing the mixture to heat, or (2) subjecting a polymer to high energy radiation.

Noncovalent associations can also occur through ionic interactions involving a targeting ligand and/or therapeutic agent and residues within a moiety on the surface of the targeted carrier, e.g., nanoparticle. Noncovalent associations can also occur through ionic interactions involving a targeting ligand and/or therapeutic agent and residues within a primer, such as charged amino acids, or through the use of a primer portion comprising charged residues that can interact with both the targeting ligand and the targeted carrier, e.g., nanoparticle, surface. For example, noncovalent conjugation can occur between a generally negatively-charged targeting ligand or moiety on a nanoparticle surface and positively-charged amino acid residues of a primer, e.g., polylysine, polyarginine and polyhistidine residues. In another example, noncovalent conjugation can occur between a generally negatively-charged targeting ligand or moiety on an intermediate linker component and positively-charged amino acid residues of a therapeutic agent.

The ligand may bind directly to the particle or liposome, i.e., the ligand is associated with the particle or liposome itself. Alternatively, indirect binding may also be effected using a hydrolizable anchor, such as a hydrolizable lipid anchor, to couple the targeting ligand or other organic moiety to the lipid/surfactant coating of the particle or liposome. Indirect binding such as that effected through biotin/avidin may also be employed for the ligand. For example, in biotin/avidin mediated targeting, the targeting ligand is coupled not to the particle or liposome, but rather coupled, in biotinylated form to the targeted tissue.

Ancillary agents that may be coupled to the targeted carriers, e.g., nanoparticles, through entrapment in the coating layer include radionuclides. Radionuclides may be either therapeutic or diagnostic; diagnostic imaging using such nuclides is well known and by targeting radionuclides to desired tissue a therapeutic benefit may be realized as well. Radionuclides for diagnostic imaging often include gamma emitters (e.g., $^{96}$Tc) and radionuclides for therapeutic purposes often include alpha emitters (e.g., $^{225}$Ac) and beta emitters (e.g., $^{90}$Y). Typical diagnostic radionuclides include $^{99m}$Tc, $^{96}$Tc, $^{95}$Tc, $^{111}$In, $^{62}$Cu, $^{64}$Cu, $^{67}$Ga, $^{68}$Ga, and $^{192}$Ir, and therapeutic nuclides include $^{225}$Ac, $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{123}$I, $^{131}$I, $^{67}$Cu, $^{105}$Rh, $^{111}$Ag, and $^{192}$Ir. The nuclide can be provided to a preformed particle in a variety of ways. For example, $^{99}$Tc-pertechnate may be mixed with an excess of stannous chloride and incorporated into the preformed emulsion of nanoparticles. Stannous oxinate can be substituted for stannous chloride. In addition, commercially available kits, such as the HM-PAO. (exametazine) kit marketed as Ceretek® by Nycomed Amersham can be used. Means to attach various radioligands to the targeted carriers of the invention are understood in the art.

Chelating agents containing metal ions for use, for example, in magnetic resonance imaging can also be employed as ancillary agents. Typically, a chelating agent containing a paramagnetic metal or superparamagnetic metal is associated with the lipids/surfactants of the coating on the particles and incorporated into the initial mixture. The chelating agent can be coupled directly to one or more of components of the coating layer. Suitable chelating agents are macrocyclic or linear chelating agents and include a variety of multi-dentate compounds including EDTA, DPTA, DOTA, and the like. These chelating agents can be coupled directly to functional groups contained in, for example, phosphatidyl ethanolamine, oleates, or any other synthetic natural or functionalized lipid or lipid soluble compound. Alternatively, these chelating agents can coupled through linking groups.

Chelating agents appropriate for use in some instances include 1,4,7,10-tetraazacyclododecane-1,4,7,10-tetraacetic acid (DOTA) and its derivatives, in particular, a methoxybenzyl derivative (MEO-DOTA) and a methoxybenzyl derivative comprising an isothiocyanate functional group (MEO-DOTA-NCS) which can then be coupled to the amino group of phosphatidyl ethanolamine or to a peptide derivatized form thereof. Derivatives of this type are described in U.S. Pat. No. 5,573,752 and other suitable chelating agents are disclosed in U.S. Pat. No. 6,056,939.

The DOTA isocyanate derivative can also be coupled to the lipid/surfactant directly or through a peptide spacer. The use of gly-gly-gly as a spacer is illustrated in the reaction scheme below. For direct coupling, the MEO-DOTA-NCS is simply reacted with phosphoethanolamine (PE) to obtain the coupled product. When a peptide is employed, for example a triglycyl link, PE is first coupled to t-boc protected triglycine. Standard coupling techniques, such as forming the activated ester of the-free acid of the t-boc-triglycine using diisopropyl carbodiimide (or an equivalent thereof) with either N-hydroxy succinimide (NHS) or hydroxybenzotriazole (HBT) are employed and the t-boc-triglycine-PE is purified.

Treatment of the t-boc-triglycine-PE with trifluoroacetic acid yields triglycine-PE, which is then reacted with excess MEO-DOTA-NCS in DMF/CHCl$_3$ at 50° C. The final product is isolated by removing the solvent, followed by rinsing the remaining solid with excess water, to remove excess solvent and any un-reacted or hydrolyzed MEO-DOTA-NCS.

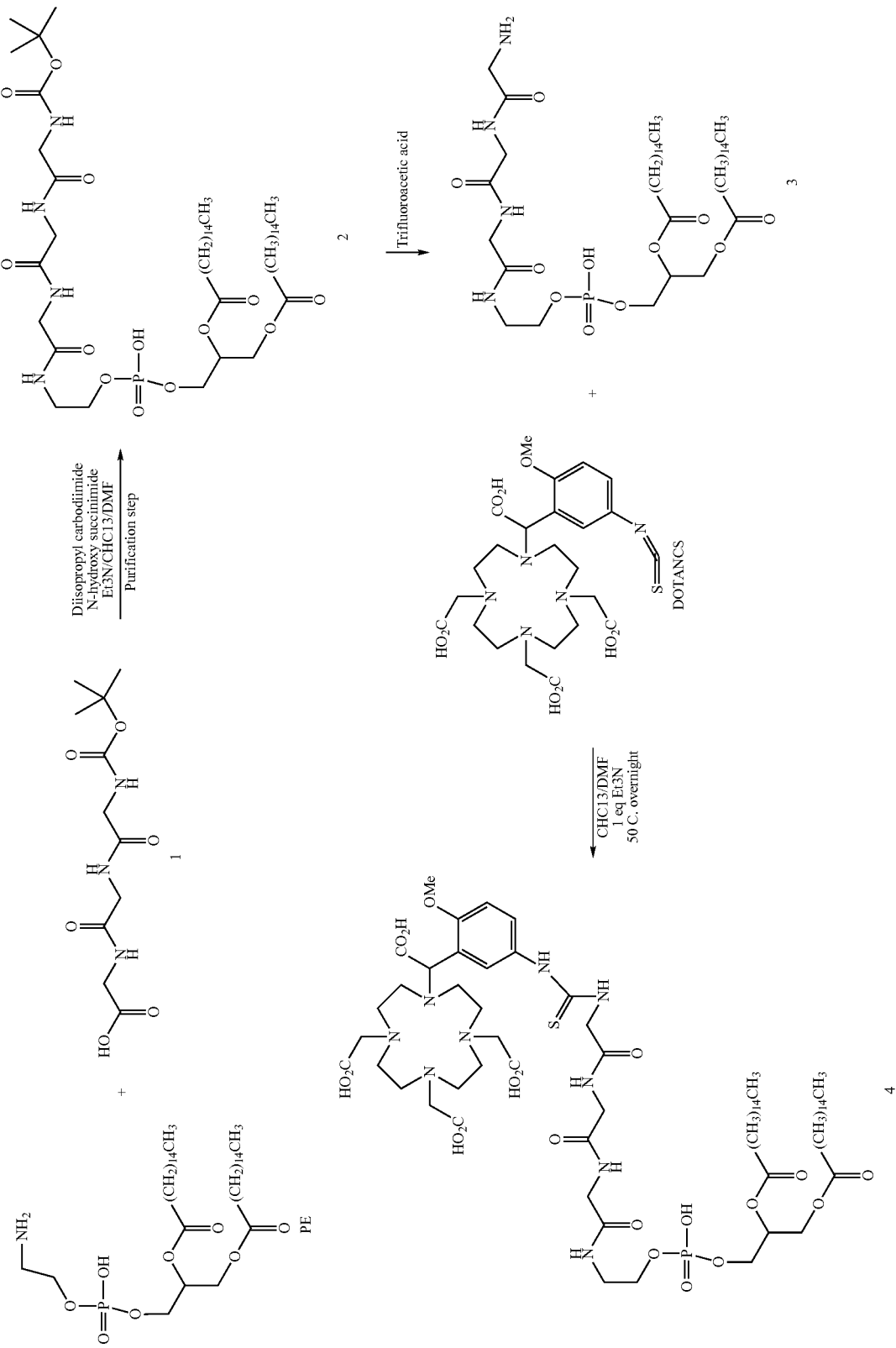

Other ancillary agents include fluorophores (such as fluorescein, dansyl, quantum dots, and the like) and infrared dyes or metals may be used in optical or light imaging (e.g., confocal microscopy and fluorescence imaging). For nuclear imaging, such as PET imaging, tosylated and $^{18}$F fluorinated compounds may be associated with the targeted carriers as ancillary agents.

In all of the foregoing cases, whether the associated moiety is a targeting ligand or therapeutic agent or an ancillary agent, the defined moiety may be non-covalently associated with the lipid/surfactant layer, may be directly coupled to the components of the lipid/surfactant layer, or may be indirectly coupled to said components through spacer moieties.

As described herein, targeting ligands and/or therapeutic agents may be chemically attached to the surface of the targeted carriers, e.g., nanoparticles, by a variety of methods depending upon the nature of the carrier complex surface. Conjugations may be performed before or after an emulsion particle is created depending upon the ligand employed. Direct chemical conjugation of ligands to proteinaceous agents often take advantage of numerous amino-groups (e.g. lysine) inherently present within the surface. Alternatively, functionally active chemical groups such as pyridyldithiopropionate, maleimide or aldehyde may be incorporated into the surface as chemical "hooks" for ligand conjugation after the particles are formed. Another common post-processing approach is to activate surface carboxylates with carbodiimide prior to ligand addition. The selected covalent linking strategy is primarily determined by the chemical nature of the ligand. Antibodies and other large proteins may denature under harsh processing conditions; whereas, the bioactivity of carbohydrates, short peptides, aptamers, drugs or peptidomimetics often can be preserved. To ensure high ligand binding integrity and maximize targeted particle avidity flexible polymer spacer arms, e.g. polyethylene glycol or simple caproate bridges, can be inserted between an activated surface functional group and the targeting ligand. These extensions can be 10 nm or longer and minimize interference of ligand binding by particle surface interactions.

Avidin-biotin interactions are extremely useful, noncovalent targeting systems that have been incorporated into many biological and analytical systems and selected in vivo applications. Avidin has a high affinity for biotin ($10^{-15}$ M) facilitating rapid and stable binding under physiological conditions. Some targeted systems utilizing this approach are administered in two or three steps, depending on the formulation. Typically in these systems, a biotinylated ligand, such as a monoclonal antibody, is administered first and "pretargeted" to the unique molecular epitopes. Next, avidin is administered, which binds to the biotin moiety of the "pre-targeted" ligand. Finally, the biotinylated emulsion is added and binds to the unoccupied biotin-binding sites remaining on the avidin thereby completing the ligand-avidin-emulsion "sandwich." The avidin-biotin approach can avoid accelerated, premature clearance of targeted agents by the reticuloendothelial system secondary to the presence of surface antibody. Additionally, avidin, with four, independent biotin binding sites provides signal amplification and improves detection sensitivity.

As used herein, the term "biotin emulsion" or "biotinylated" with respect to conjugation to a biotin emulsion or biotin agent is intended to include biotin, biocytin and other biotin derivatives and analogs such as biotin amido caproate N-hydroxysuccinimide ester, biotin 4-amidobenzoic acid, biotinamide caproyl hydrazide and other biotin derivatives and conjugates. Other derivatives include biotin-dextran, biotin-disulfide N-hydroxysuccinimide ester, biotin-6 amido quinoline, biotin hydrazide, d-biotin-N hydroxysuccinimide ester, biotin maleimide, d-biotin p-nitrophenyl ester, biotinylated nucleotides and biotinylated amino acids such as N, epsilon-biotinyl-1-lysine. The term "avidin emulsion" or "avidinized" with respect to conjugation to an avidin emulsion or avidin agent is intended to include avidin, streptavidin and other avidin analogs such as streptavidin or avidin conjugates, highly purified and fractionated species of avidin or streptavidin, and non-amino acid or partial-amino acid variants, recombinant or chemically synthesized avidin.

Antibodies, particularly monoclonal antibodies, may also be used as site-targeting ligands directed to molecular epitopes expressed on or in neovasculature. Immunoglobin-γ(IgG) class monoclonal antibodies have been conjugated to nanoparticles and other carriers to provide active, site-specific targeting. Generally, these proteins are symmetric glycoproteins (MW ca. 150,000 Daltons) composed of identical pairs of heavy and light chains. Hypervariable regions at the end of each of two arms provide identical antigen-binding domains. A variably sized branched carbohydrate domain is attached to complement-activating regions, and the hinge area contains particularly accessible interchain disulfide bonds that may be reduced to produce smaller fragments.

In some instances, monoclonal antibodies are used in the antibody compositions of the invention. Monoclonal antibodies specific for selected antigens on the surface of neovasculature cells may be readily generated using conventional techniques (see, for example, U.S. Pat. Nos. RE 32,011, 4,902,614, 4,543,439, and 4,411,993). Hybridoma cells can be screened immunochemically for production of antibodies specifically reactive with an antigen, and monoclonal antibodies can be isolated. Other techniques may also be utilized to construct monoclonal antibodies (see, for example, Huse et al. (1989) *Science* 246:1275-1281; Sastry et al. (1989) *Proc. Natl. Acad. Sci. USA* 86:5728-5732; Alting-Mees et al. (1990) *Strategies in Molecular Biology* 3:1-9).

Within the context of the present invention, antibodies are understood to include various kinds of antibodies, including, but not necessarily limited to, naturally occurring antibodies, monoclonal antibodies, polyclonal antibodies, antibody fragments that retain antigen binding specificity (e.g., Fab, and F(ab')$_2$) and recombinantly produced binding partners, single domain antibodies, hybrid antibodies, chimeric antibodies, single-chain antibodies, human antibodies, humanized antibodies, and the like. Generally, antibodies are understood to be reactive against a selected antigen of a cell if they bind with an affinity (association constant) of greater than or equal to $10^7$ M$^{-1}$. Antibodies against selected antigens for use with the emulsions may be obtained from commercial sources.

Further description of the various kinds of antibodies of use as site-targeting ligands in the invention is provided herein, in particular, later in this Compositions section.

The targeted carriers of use in the present invention also employ targeting agents that are ligands other than an antibody or fragment thereof. For example, polypeptides, like antibodies, may have high specificity and epitope affinity for use as targeting ligands. These may be small oligopeptides, having, for example, 5 to 10 amino acid, specific for a unique receptor sequences (such as, for example, the RGD epitope of the platelet GIIbIIIa receptor) or larger, biologically active hormones such as cholecystokinin. Smaller peptides potentially have less inherent immunogenicity than nonhumanized murine antibodies. Peptides or peptide (nonpeptide) analogues of cell adhesion molecules, cytokines, selectins, cadherins, Ig superfamily, integrins and the like may be utilized for targeted therapeutic delivery as long as they direct the targeted carrier to the desired target, e.g., expanded vasa vasorum.

In some instances, the ligand is a non-peptide organic molecule, such as those described in U.S. Pat. No. 6,130,231 (for example as set forth in formula 1); U.S. Pat. Nos. 6,153, 628; 6,322,770; and PCT publications WO 01/97848 and WO 03/062198. "Non-peptide" moieties in general are those other than compounds which are simply polymers of amino acids, either gene encoded or non-gene encoded. Thus, "non-peptide ligands" are moieties which are commonly referred to as "small molecules" lacking in polymeric character and characterized by the requirement for a core structure other than a polymer of amino acids. The non-peptide ligands useful in the invention may be coupled to peptides or may include peptides coupled to portions of the ligand which are responsible for affinity to the target site, but it is the non-peptide regions of this ligand which account for its binding ability. For example, non-peptide ligands specific for the $\alpha_v\beta_3$ integrin are described in U.S. Pat. Nos. 6,130,231 and 6,153,628. Targeting ligands may also include carbohydrates, glycoproteins, and polysaccharides.

Aptamers are high affinity, high specificity RNA or DNA-based ligands produced by in vitro selection experiments (SELEX: systematic evolution of ligands by exponential enrichment). Aptamers are generated from random sequences of 20 to 30 nucleotides, selectively screened by absorption to molecular antigens or cells, and enriched to purify specific high affinity binding ligands. To enhance in vivo stability and utility, aptamers are generally chemically modified to impair nuclease digestion and to facilitate conjugation with drugs, labels or particles. Other, simpler chemical bridges often substitute nucleic acids not specifically involved in the ligand interaction. In solution aptamers are unstructured but can fold and enwrap target epitopes providing specific recognition. The unique folding of the nucleic acids around the epitope affords discriminatory intermolecular contacts through hydrogen bonding, electrostatic interaction, stacking, and shape complementarity. In comparison with protein-based ligands, generally aptamers are stable, are more conducive to heat sterilization, and have lower immunogenicity. Aptamers are currently used to target a number of clinically relevant pathologies including angiogenesis, activated platelets, and solid tumors and their use is increasing. The clinical effectiveness of aptamers as targeting ligands for therapeutic targeted carriers may be dependent upon the impact of the negative surface charge imparted by nucleic acid phosphate groups on clearance rates.

It is also possible to use what has been referred to as a "primer material" to couple specific binding species to the targeted carriers for certain applications. As used herein, "primer material" refers to any constituent or derivatized constituent incorporated into the emulsion lipid surfactant layer that could be chemically utilized to form a covalent bond between the particle, for example, and a targeting ligand or a component of the targeting ligand such as a subunit thereof.

Thus, the targeting ligand may be immobilized on the encapsulating lipid monolayer by direct adsorption to the oil/aqueous interface or using a primer material. A primer material may be any surfactant compatible compound incorporated in the carrier complex, e.g., particle, to chemically couple with or adsorb a specific binding or targeting species. For example, an emulsion can be formed with an aqueous continuous phase and a targeting ligand adsorbed or conjugated to the primer material at the interface of the continuous and discontinuous phases. Naturally occurring or synthetic polymers with amine, carboxyl, mercapto, or other functional groups capable of specific reaction with coupling agents and highly charged polymers may be utilized in the coupling process. The targeting ligand (e.g. antibody) may be immobilized on the emulsion particle surface by direct adsorption or by chemical coupling. Examples of targeting ligands which can be immobilized by direct adsorption include small peptides, peptidomimetics, or polysaccharide-based agents. To make such an emulsion the specific binding species may be suspended or dissolved in the aqueous phase prior to formation of the emulsion. Alternatively, the targeting ligand may be added after formation of the emulsion and incubated with gentle agitation at room temperature (about 25° C.) in a pH 7.0 buffer (typically phosphate buffered saline) for 1.2 to 18 hours.

Where the targeting ligand is to be coupled to a primer material, conventional coupling techniques may be used. The targeting ligand may be covalently bonded to primer material with coupling agents using methods which are known in the art. Primer materials may include phosphatidylethanolamine (PE), N-caproylamine-PE, n-dodecanylamine, phosphatidylthioethanol,N-1,2-diacyl-sn-glycero-3-phosphoethanolamine-N-[4-(p-maleimidophenyl)butyramide], 1,2-diacyl-sn-glycero-3-phosphoethanolamine-N-[4-(p-maleirnidomethyl)cyclohexane-carboxylate], 1,2-diacyl-sn-glycero-3-phosphoethanolamine-N-[3-(2-pyridyldithio) propionate], 1,2-diacyl-sn-glycero-3-phosphoethanolamine-N[PDP(polyethylene glycol)2000], N-succinyl-PE, N-glutaryl-PE, N-dodecanyl-PE, N-biotinyl-PE, or N-caproyl-PE. Additional coupling agents include, for example, use a carbodiimide or an aldehyde having either ethylenic unsaturation or having a plurality of aldehyde groups. Further description of additional coupling agents appropriate for use is provided herein, in particular, later in this Compositions section.

Covalent bonding of a targeting ligand to the primer material can be carried out with the reagents provided herein and with others by conventional, well-known reactions, for example, in the aqueous solutions at a neutral pH, at temperatures of less than 25° C. for 1 hour to overnight. Examples of linkers for coupling a ligand, including non-peptide ligands, are known in the art.

In certain embodiments, the targeting ligands may be incorporated in the present compositions via non-covalent associations. As known in the art, non-covalent association is generally a function of a variety of factors, including, for example, the polarity of the involved molecules, the charge (positive or negative), if any, of the involved molecules, the extent of hydrogen bonding through the molecular network, and the like. Non-covalent bonds are generally selected from the group consisting of ionic interaction, dipole-dipole interaction, hydrogen bonds, hydrophilic interactions, van der Waal's forces, and any combinations thereof.

Non-covalent interactions may be used to couple the targeting ligand to the lipid or directly to another component at the surface of the lipid-encapsulated carrier complex. For example, the amino acid sequence Gly-Gly-His may be bound to the surface of an lipid-encapsulated nanoparticles, preferably by a primer material, such as PEG, and copper, iron or vanadyl ion may then be added. Proteins, such as antibodies which contain histidine residues, may then bind to the lipid-encapsulated particles via an ionic bridge with the copper ion, as described in U.S. Pat. No. 5,466,467. An example of hydrogen bonding involves cardiolipin lipids which can be incorporated into the lipid compositions. Examples of non-covalent associations can also occur through ionic interactions involving a targeting ligand and residues within a primer or on a carrier complex, such as charged amino acids, include those between a generally negatively-charged target cell directed moiety or moiety on an lipid-encapsulated carrier surface and positively-charged amino acid residues of a primer, e.g., polylysine, polyarginine and polyhistidine residues.

The free end of the hydrophilic primer, such as polyethylene glycol ethylamine, which contains a reactive group, such as an amine or hydroxyl group, could be used to couple a targeting ligand. For example, polyethylene glycol ethylamine may be reacted with N-succinimidylbiotin or p-nitrophenylbiotin to introduce onto the spacer a useful coupling group. For example, biotin may be coupled to the spacer and this will readily bind non-covalently proteins or other targeting ligands bearing avidin or streptavidin.

Emulsifying and/or solubilizing agents may also be used in conjunction with emulsions. Such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer, peanut oil, palmitic acid, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax. All lipids with perfluoro fatty acids as a component of the lipid in lieu of the saturated or unsaturated hydrocarbon fatty acids found in lipids of plant or animal origin may be used. Suspending and/or viscosity-increasing agents that may be used with emulsions include, but are not limited to, acacia, agar, alginic acid, aluminum mono-stearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

As described herein, targeted carriers, e.g., nanoparticles, may incorporate on the particle paramagnetic or super paramagnetic elements including but not limited to gadolinium, magnesium, iron, manganese in their native or in a chemically complexed form. Similarly, radioactive nuclides including positron-emitters, gamma-emitters, beta-emitters, alpha-emitters in their native or chemically-complexed form may be included on or in the particles. In some instances, adding of these moieties may permit the additional use of clinical imaging modalities such as MRI, PET, and nuclear medicine imaging techniques in combination with the targeted delivery of a therapeutic agent.

In addition, optical imaging, which refers to the production of visible representations of tissue or regions of a patient produced by irradiating those tissues or regions of a patient with electromagnetic energy in the spectral range between ultraviolet and infrared, and analyzing either the reflected, scattered, absorbed and/or fluorescent energy produced as a result of the irradiation, may be combined with the targeted delivery of a therapeutic agent. Examples of optical imaging include, but are not limited to, visible photography and variations thereof, ultraviolet images, infrared images, fluorimetry, holography, visible microscopy, fluorescent microscopy, spectrophotometry, spectroscopy, fluorescence polarization and the like.

Photoactive agents, i.e. compounds or materials that are active in light or that responds to light, including, for example, chromophores (e.g., materials that absorb light at a given wavelength), fluorophores (e.g., materials that emit light at a given wavelength), photosensitizers (e.g., materials that can cause necrosis of tissue and/or cell death in vitro and/or in vivo), fluorescent materials, phosphorescent materials and the like, that may be used in diagnostic or therapeutic applications. "Light" refers to all sources of light including the ultraviolet (UV) region, the visible region and/or the infrared (IR) region of the spectrum. Suitable photoactive agents that may be used in the present invention have been described by others (for example, U.S. Pat. No. 6,123,923).

In addition to that described elsewhere herein, following is further description of the various kinds of antibodies appropriate for use as targeting ligands in and/or with the targeted carriers of the invention.

Bivalent F(ab')$_2$ and monovalent F(ab) fragments can be used as ligands and these are derived from selective cleavage of the whole antibody by pepsin or papain digestion, respectively. Antibodies can be fragmented using conventional techniques and the fragments (including "Fab" fragments) screened for utility in the same manner as described above for whole antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)$_2$), which are capable of selectively reacting with a designated antigen or antigen family. Methods of producing Fab fragments of antibodies are known within the art and include, for example, proteolysis, and synthesis by recombinant techniques. For example, F(ab')$_2$ fragments can be generated by treating antibody with pepsin. The resulting F(ab')$_2$ fragment can be treated to reduce disulfide bridges to produce Fab' fragments. "Fab" antibodies may be divided into subsets analogous to those described herein, i.e., "hybrid Fab", "chimeric Fab", and "altered Fab". Elimination of the Fc region greatly diminishes the immunogenicity of the molecule, diminishes nonspecific liver uptake secondary to bound carbohydrate, and reduces complement activation and resultant antibody-dependent cellular toxicity. Complement fixation and associated cellular cytotoxicity can be detrimental when the targeted site must be preserved or beneficial when recruitment of host killer cells and target-cell destruction is desired.

Most monoclonal antibodies are of murine origin and are inherently immunogenic to varying extents in other species. Humanization of murine antibodies through genetic engineering has lead to development of chimeric ligands with improved biocompatibility and longer circulatory half-lives. Antibodies used in the invention include those that have been humanized or made more compatible with the individual to which they will be administered. In some cases, the binding affinity of recombinant antibodies to targeted molecular epitopes can be improved with selective site-directed mutagenesis of the binding idiotype. Methods and techniques for such genetic engineering of antibody molecules are known in the art. By "humanized" is meant alteration of the amino acid sequence of an antibody so that fewer antibodies and/or immune responses are elicited against the humanized antibody when it is administered to a human. For the use of the antibody in a mammal other than a human, an antibody may be converted to that species format.

Phage display techniques may be used to produce recombinant human monoclonal antibody fragments against a large range of different antigens without involving antibody-producing animals. In general, cloning creates large genetic libraries of corresponding DNA (cDNA) chains deducted and synthesized by means of the enzyme "reverse transcriptase" from total messenger RNA (mRNA) of human B lymphocytes. By way of example, immunoglobulin cDNA chains are amplified by polymerase chain reaction (PCR) and light and heavy chains specific for a given antigen are introduced into a phagemid vector. Transfection of this phagemid vector into the appropriate bacteria results in the expression of a single chain Fv (scFv) immunoglobulin molecule on the surface of the bacteriophage. Bacteriophages expressing specific immunoglobulin are selected by repeated immunoadsorption/phage multiplication cycles against desired antigens (e.g., proteins, peptides, nuclear acids, and sugars). Bacteriophages strictly specific to the target antigen are introduced into an appropriate vector, (e.g., *Escherichia coli*, yeast, cells) and amplified by fermentation to produce large amounts of human antibody fragments, generally with structures very similar to natural antibodies. Phage display techniques are known in the art and have permitted the production of unique ligands for targeting and therapeutic applications.

Polyclonal antibodies against selected antigens may be readily generated by one of ordinary skill in the art from a variety of warm-blooded animals such as horses, cows, various fowl, rabbits, mice, or rats. In some cases, human polyclonal antibodies against selected antigens may be purified from human sources.

As used herein, a "single domain antibody" (dAb) is an antibody which is comprised of a $V_H$ domain, which reacts immunologically with a designated antigen. A dAb does not contain a $V_L$ domain, but may contain other antigen binding domains known to exist in antibodies, for example, the kappa and lambda domains. Methods for preparing dAbs are known in the art. See, for example, Ward et al. (1989) *Nature* 341: 544-546. Antibodies may also be comprised of $V_H$ and $V_L$ domains, as well as other known antigen binding domains. Examples of these types of antibodies and methods for their preparation are known in the art (see, e.g., U.S. Pat. No. 4,816,467).

Further exemplary antibodies include "univalent antibodies", which are aggregates comprised of a heavy chain/light chain dimer bound to the Fc (i.e., constant) region of a second heavy chain. This type of antibody generally escapes antigenic modulation. See, e.g., Glennie et al. (1982) *Nature* 295:712-714.

"Hybrid antibodies" are antibodies wherein one pair of heavy and light chains is homologous to those in a first antibody, while the other pair of heavy and light chains is homologous to those in a different second antibody. Typically, each of these two pairs will bind different epitopes, particularly on different antigens. This results in the property of "divalence", i.e., the ability to bind two antigens simultaneously. Such hybrids may also be formed using chimeric chains, as set forth herein.

The invention also encompasses "altered antibodies", which refers to antibodies in which the naturally occurring amino acid sequence in a vertebrate antibody has been varied. Utilizing recombinant DNA techniques, antibodies can be redesigned to obtain desired characteristics. The possible variations are many, and range from the changing of one or more amino acids to the complete redesign of a region, for example, the constant region. Changes in the variable region may be made to alter antigen binding characteristics. The antibody may also be engineered to aid the specific delivery of an emulsion to a specific cell or tissue site. The desired alterations may be made by known techniques in molecular biology, e.g., recombinant techniques, site directed mutagenesis, and other techniques.

"Chimeric antibodies", are antibodies in which the heavy and/or light chains are fusion proteins. Typically the constant domain of the chains is from one particular species and/or class, and the variable domains are from a different species and/or class. The invention includes chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes selected antigens on the surface of targeted cells and/or tissues. See, for example, Morrison et al. (1985) *Proc. Natl. Acad. Sci. U.S.A.* 81:6851; Takeda et al. (1985) *Nature* 314: 452; U.S. Pat. Nos. 4,816,567 and 4,816,397; European Patent Publications EP171496 and EP173494; United Kingdom patent GB 2177096B.

Bispecific antibodies may contain a variable region of an anti-target site antibody and a variable region specific for at least one antigen on the surface of the targeted carrier complex. In other cases, bispecific antibodies may contain a variable region of an anti-target site antibody and a variable region specific for a linker molecule. Bispecific antibodies may be obtained forming hybrid hybridomas, for example by somatic hybridization. Hybrid hybridomas may be prepared using the procedures known in the art such as those disclosed in Staerz et al. (1986, *Proc. Natl. Acad. Sci. U.S.A.* 83:1453) and Staerz et al. (1986, *Immunology Today* 7:241). Somatic hybridization includes fusion of two established hybridomas generating a quadroma (Milstein et al. (1983) *Nature* 305: 537-540) or fusion of one established hybridoma with lymphocytes derived from a mouse immunized with a second antigen generating a trioma (Nolan et al. (1990) *Biochem. Biophys. Acta* 1040:1-11). Hybrid hybridomas are selected by making each hybridoma cell line resistant to a specific drug-resistant marker (De Lau et al. (1989) *J. Immunol. Methods* 117:1-8), or by labeling each hybridoma with a different fluorochrome and sorting out the heterofluorescent cells (Karawajew et al. (1987) *J. Immunol. Methods* 96:265-270).

Bispecific antibodies may also be constructed by chemical means using procedures such as those described by Staerz et al. (1985) *Nature* 314:628 and Perez et al. (1985) *Nature* 316:354. Chemical conjugation may be based, for example, on the use of homo- and heterobifunctional reagents with E-amino groups or hinge region thiol groups. Homobifunctional reagents such as 5,5'-dithiobis(2-nitrobenzoic acid) (DNTB) generate disulfide bonds between the two Fabs, and O-phenylenedimaleimide (O-PDM) generate thioether bonds between the two Fabs (Brenner et al. (1985) *Cell* 40:183-190, Glennie et al. (1987) *J. Immunol.* 139:2367-2375). Heterobifunctional reagents such as N-succinimidyl-3-(2-pyridyl-ditio) propionate (SPDP) combine exposed amino groups of antibodies and Fab fragments, regardless of class or isotype (Van Dijk et al. (1989) *Int. J. Cancer* 44:738-743).

Bifunctional antibodies may also be prepared by genetic engineering techniques. Genetic engineering involves the use of recombinant DNA based technology to ligate sequences of DNA encoding specific fragments of antibodies into plasmids, and expressing the recombinant protein. Bispecific antibodies can also be made as a single covalent structure by combining two scFv fragments using linkers (Winter et al.

(1991) *Nature* 349:293-299); as leucine zippers coexpressing sequences derived from the transcription factors fos and jun (Kostelny et al. (1992) *J. Immunol.* 148:1547-1553); as helix-turn-helix coexpressing an interaction domain of p53 (Rheinnecker et al. (1996) *J. Immunol.* 157:2989-2997), or as diabodies (Holliger et al. (1993) *Proc. Natl. Acad. Sci. U.S.A.* 90:6444-6448).

In addition to that described elsewhere herein, following is further description of coupling agents appropriate for use in coupling a primer material, for example, to a specific binding or targeting ligand. Additional coupling agents use a carbodiimide such as 1-ethyl-3-(3-N,N dimethylaminopropyl) carbodiimide hydrochloride or 1-cyclohexyl-3-(2-morpholinoethyl)carbodiimide methyl-p-toluenesulfonate. Other suitable coupling agents include aldehyde coupling agents having either ethylenic unsaturation such as acrolein, methacrolein, or 2-butenal, or having a plurality of aldehyde groups such as glutaraldehyde, propanedial or butanedial. Other coupling agents include 2-iminothiolane hydrochloride, bifunctional N-hydroxysuccinimide esters such as disuccinimidyl substrate, disuccinimidyl tartrate, bis[2-(succinimidooxycarbonyloxy)ethyl]sulfone, disuccinimidyl propionate, ethylene glycolbis(succinimidyl succinate); heterobifunctional reagents such as N-(5-azido-2-nitrobenzoyloxy)succinimide, p-azidophenylbromide, p-azidophenylglyoxal, 4-fluoro-3-nitrophenylazide, N-hydroxysuccinimidyl-4-azidobenzoate, m-maleimidobenzoyl N-hydroxysuccinimide ester, methyl-4-azidophenylglyoxal, 4-fluoro-3-nitrophenyl azide, N-hydroxysuccinimidyl-4-azidobenzoate hydrochloride, p-nitrophenyl 2-diazo-3,3,3-trifluoropropionate, N-succinimidyl-6-(4'-azido-2'-nitrophenylamino)hexanoate, succinimidyl 4-(N-maleimidomethyl)cyclohexane-1-carboxylate, succinimidyl 4-(p-maleimidophenyl)butyrate, N-succinimidyl(4-azidophenyldithio)propionate, N-succinimidyl 3-(2-pyridyldithio)propionate, N-(4-azidophenylthio)phthalamide; homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like.

The targeted carriers of the present invention may be prepared by various techniques described herein and known in the art. In a typical procedure for preparing nanoparticulate emulsions as targeted carriers of the invention, the core oil or oils and the components of the lipid/surfactant coating are fluidized in aqueous medium to form an emulsion. The functional components of the surface layer may be included in the original emulsion, or may later be covalently coupled to the surface layer subsequent to the formation of the nanoparticle emulsion. In one particular instance, for example, where a nucleic acid targeting agent or therapeutic agent is to be included, the coating may employ a cationic surfactant and the nucleic acid adsorbed to the surface after the particle is formed.

Generally, the emulsifying process involves directing high pressure streams of mixtures containing the aqueous solution, a primer material or the targeting ligand, the core oil or oils and a surfactant (if any) so that they impact one another to produce emulsions of narrow particle size and distribution. The MICROFLUIDIZER apparatus (Microfluidics, Newton, MA) can be used to make the preferred emulsions. The apparatus is also useful to post-process emulsions made by sonication or other conventional methods. Feeding a stream of emulsion droplets through the MICROFLUIDIZER apparatus yields formulations small size and narrow particle size distribution.

An alternative method for making the emulsions involves sonication of a mixture of oil(s) and an aqueous solution containing a suitable primer material and/or targeting ligand. Generally, these mixtures include a surfactant. Cooling the mixture being emulsified, minimizing the concentration of surfactant, and buffering with a saline buffer will typically maximize both retention of specific binding properties of the targeting ligand and the coupling capacity of the primer material. These techniques generally provide excellent emulsions with high activity per unit of absorbed primer material or targeting ligand.

In some instances, when high concentrations of a primer material or targeting ligand are to be coated on lipid emulsions, the mixture should be heated during sonication and have a relatively low ionic strength and moderate to low pH. Too low an ionic strength, too low a pH or too much heat may cause some degradation or loss of all of the useful binding properties of the targeting ligand or the coupling capacity of the primer material. Careful control and variation of the emulsification conditions can optimize the properties of the primer material or the targeting ligand while obtaining high concentrations of coating.

The emulsion particle sizes can be controlled and varied by modification of the emulsification techniques and the chemical components. Techniques and equipment for determining particle sizes are known in the art and include, but not limited to, laser light scattering and an analyzer for determining laser light scattering by particles.

When appropriately prepared, the targeted carriers contain a multiplicity of functional such agents at their outer surface. For example, nanoparticles typically contain hundreds or thousands of molecules of the therapeutic agent, targeting ligand, radionuclide, and/or imaging contrast agent. For MRI contrast agents, the number of copies of a component to be coupled to the nanoparticle is typically in excess of 5,000 copies per particle, more preferably 10,000 copies per particle, still more preferably 30,000, and still more preferably 50,000-100,000 or more copies per particle. The number of targeting ligands per particle is typically less, of the order of several hundred while the concentration of PET contrast agents, fluorophores, radionuclides, and therapeutic agents is also variable.

The emulsions can be prepared in a range of methods depending on the nature of the components. In a typical procedure, used for illustrative purposes only, the following procedure is set forth: perfluorooctylbromide (PFOB, 20% v/v), safflower oil (2% w/v), a surfactant co-mixture (2.0%, w/v), glycerin (1.7%, w/v) and water representing the balance is prepared. The surfactant co-mixture includes 58 mole % lecithin, 10 mole % cholesterol, 1.8 mole % phosphatidylethanolamine, 0.1 mole % peptidomimetic vitronectin antagonist conjugated to $PEG_{2000}$-phosphatidylethanolamine (targeting ligand), and 30 mole % of gadolinium diethylenetriamine-pentaacetic acid-bis-oleate dissolved in chloroform. A therapeutic agent is added in titrated amounts between 0.01 and 50 mole % of the 2% surfactant layer, between 0.01 and 20 mole % of the 2% surfactant layer, between 0.01 and 10 mole % of the 2% surfactant layer, between 0.01 and 5.0 mole % of the 2% surfactant layer, preferably between 0.2 and 2.0 mole % of the 2% surfactant layer. The chloroform-lipid mixture is evaporated under reduced pressure, dried in a 50° C. vacuum oven overnight and dispersed into water by sonication. The suspension is transferred into a blender cup (for example, from Dynamics Corporation of America) with oil in distilled or deionized water and emulsified for 30 to 60 seconds. The emulsified mixture is transferred to a Microfluidics emulsifier and continuously processed at 20,000 PSI for four minutes. The completed emulsion is vialed, blanketed with nitrogen and sealed with stopper crimp seal until use. Control emulsions can be prepared identically excluding the therapeutic agent and/or the targeting ligand from the surfactant co-mixture. Particle sizes are generally determined in triplicate at 37° C. with a laser light scattering submicron particle size analyzer (Malvern Zetasizer 4, Malvern Instruments Ltd., Southborough, Mass.), which indicate tight and highly reproducible size distribution. Unincorporated therapeutic agent can be removed from the emulsion by dialysis or ultrafiltration techniques.

Kits

The targeted carriers of the invention may be prepared and used directly in the methods of the invention, or the components of the targeted carriers may be supplied in the form of kits. The kits may comprise the untargeted composition containing at least one therapeutic agent and all of the desired ancillary materials in buffer or in lyophilized form. The kits may comprise the pre-prepared targeted composition containing at least one therapeutic agent and all of the desired ancillary materials and targeting materials in buffer or in lyophilized form. Alternatively, the kits may include a form of the targeted carrier which lacks the targeting agent which is supplied separately or the kits may include a form of the targeted carrier which lacks the therapeutic agent which is supplied separately. Under these circumstances, typically, the component(s) for the targeted carrier will contain a reactive group, such as a maleimide group, which, when the component is mixed with the targeting agent and/or therpeutic agent, effects the binding of the targeting agent and/or the therapeutic agent to the targeted carrier itself. A separate container may also provide additional reagents useful in effecting the coupling. Alternatively, the component(s) for the targeted carrier may contain reactive groups which bind to linkers coupled to the desired component(s) to be supplied separately which itself contains a reactive group. A wide variety of approaches to constructing an appropriate kit may be envisioned. Individual components which make up the ultimate targeted carrier may thus be supplied in separate containers, or the kit may simply contain reagents for combination with other materials which are provided separately from the kit itself.

A non-exhaustive list of combinations might include: targeted carrier preparations that contain, in their lipid-surfactant layer, the therapeutic agent and an ancillary component, if any, such as a fluorophore or chelating agent and reactive moieties for coupling to the targeting ligand; the converse where the targeted carrier is coupled to targeting ligand and contains reactive groups for coupling to the therapeutic agent and to an ancillary material, if any; emulsions which contain both targeting ligand and therapeutic agent and possibly a chelating agent but wherein the metal to be chelated is either supplied in the kit or independently provided by the user; preparations of the nanoparticles comprising the surfactant/lipid layer where the materials in the lipid layer contain different reactive groups, one set of reactive groups for a targeted ligand, one set of reactive groups for a therapeutic agent and another set of reactive groups for an ancillary agent; preparation of targeted carriers containing any of the foregoing combinations where the reactive groups are supplied by a linking agent.

The following Examples are offered to illustrate but not to limit the invention.

EXAMPLE 1

Targeted Atherosclerosis Treatment—Primary Prevention Strategy

A. Nanoparticulate Formulations and Model System

Emulsions of paramagnetic perfluorocarbon nanoparticles targeted to $\alpha_v\beta_3$-integrins for use in the present invention were prepared as described in Winter et al. (2003) *Circulation* 108:2270-2274. In general, the nanoparticulate emulsions were comprised of 20% (v/v) perfluorooctylbromide (PFOB; Minnesota Manufacturing and Mining), 2% (w/v) safflower oil, 2% (w/v) of a surfactant co-mixture, 1.7% (w/v) glycerin and water for the balance. The surfactant co-mixture included 58 mole % lecithin (Avanti Polar Lipids, Inc.), 10 mole % cholesterol (Sigma Chemical Co., St. Louis, Mo.), 0.1 mole % peptidomimetic vitronectin antagonist (U.S. Pat. No. 6,322,770) conjugated to PEG$_2$000-phosphatidylethanolamine (Avanti Polar Lipids, Inc.), 1.8 mole % phosphatidylethanolamine (Avanti Polar Lipids, Inc.), and 30 mole % of gadolinium diethylene-triamine-pentaacetic acid-bis-oleate ($Gd^{3+}$, Gateway Chemical Technologies) (U.S. Pat. No. 5,571,498).

Nanoparticulate formulations for use in local delivery of fumagillin included 0.2 mole % of fumagillin in the surfactant mixture at the proportionate expense of lecithin. Nontargeted nanoparticles excluded the integrin homing ligand, which was replaced in the surfactant mixture by an equivalent increase in phosphatidylethanolamine.

The surfactant components were prepared as described in Lanza et al. (2002) *Circulation* 106:2842-2847 and in Winter et al. (2003) *Circulation* 108:2270-2274, combined with PFOB, safflower oil and distilled deionized water. The mixture was emulsified in a M110S Microfluidics emulsifier (Microfluidics, Inc, Newton, Mass.) at 20,000 PSI for four minutes. Particle sizes were determined at 37° C. with a laser light scattering submicron particle analyzer (Malvern Instruments, Malvern, Worcestershire, UK). The concentrations of $Gd^{3+}$ and nanoparticles in the emulsion were measured and the number of $Gd^{3+}$-complexes per nanoparticle was calculated.

Fumagillin nanoparticle emulsions (250 µl) were dialyzed in 60,000 MW cutoff dialysis tubing against 3.5 ml of releasing medium (0.9% NaCl, 0.2 mg/ml human serum albumin and 0.05% sodium azide) and continuously agitated at 37° C. The releasing medium was replaced daily and analyzed for released fumagillin concentration. Fumagillin was analyzed by reverse-phase HPLC (Waters Corporation). Chromatography was performed using a Waters Novapak $C_{18}$, 60 Å, 4 µm reversed-phase column (3.9×150 mm) with an isocratic 50% acetonitrile/0.05% of phosphoric acid mobile phase (1 ml/min at ambient temperature).

To induce atherosclerosis, male New Zealand White rabbits (Charles River Laboratories) were fed a 0.5% cholesterol diet (Purina Mills) for ~80 days. At baseline, all animals were anesthetized with 1 to 2%, isoflurane and imaged by magnetic resonance imaging (MRI) at 1.5 T. Following baseline MRI, rabbits were injected via the ear vein with either $\alpha_v\beta_3$-targeted fumagillin nanoparticles (n=5), $\alpha_v\beta_3$-targeted nanoparticles without fumagillin (n=6) or nontargeted fumagillin nanoparticles (n=6) at 1 ml/kg. Four hours after nanoparticle injections, rabbits were re-imaged by MRI to assess the magnitude and distribution of signal enhancement.

After nanoparticle administration, all rabbits were placed on a normal rabbit chow diet (Purina Mills). One week later, the level of angiogenesis in each animal was reassessed by molecular imaging with $\alpha_v\beta_3$-targeted paramagnetic nanoparticles (1.0 ml/kg; no drug) with the same imaging protocol utilized during treatment (i.e., baseline MRI, injection of targeted-contrast followed by second MR image 4 hours postinjection).

Blood samples were drawn from the ear vein at baseline and following the last imaging session (one week later) to assess clinical chemistries and hematology.

B. Histology Procedures and Magnetic Resonance Imaging

Magnetic resonance imaging was performed at 1.5 T, a clinically relevant field strength, using a clinical scanner (NT Intera CV, Philips Medical Systems) and a quadrature birdcage radiofrequency receive coil. Anesthetized rabbits were scanned before and four hours after intravenous injection of paramagnetic nanoparticles. Multislice $T_1$-weighted, spin-echo, fat-suppressed, black-blood images were acquired of the entire abdominal aorta from the renal arteries to the diaphragm (TR=380 ms, TE=11 ms, 250×250-μm in-plane resolution, 5-mm slice thickness, number of signals averaged=8).

MRI signal enhancement of the aortic wall was calculated using a custom, semi-automated segmentation program as described in Winter et al. (2003) *Circulation* 108:2270-2274. Briefly, the aortic lumen was defined in each 2-dimensional image with a seeded region-growing algorithm. The aortic wall was segmented with dilation of the luminal mask followed by automated thresholding. Image intensity was normalized relative to a fiduciary marker (a gadolinium-DTPA/saline solution in a test tube phantom) placed within the field of view. The signal enhancement of the aortic wall was calculated slice-by-slice with respect to the average MRI intensity for that animal at baseline. All MR signal data were statistically analyzed using ANOVA procedures (i.e., General Linear Models), and treatment group mean separation for significant model effects utilizing Duncan's multiple-range tests (p <0.05, SAS, Inc.).

For histology and immunohistology analysis, formalin-fixed samples from each quarter of the aorta between the diaphragm and renal arteries were paraffin-embedded, sectioned (4 μm) and stained with hematoxylin and eosin. Analogous aortic segments were obtained near the diaphragm where the development of early neointimal plaques was most consistently noted. These segments were stained for the expression of $\alpha_v\beta_3$-integrin on angiogenic vessels (LM-609, Chemicon International, Inc) and CD31 (Chemicon International, Inc), an abundant endothelial cell marker, using routine methods as described, for example in Winter et al. (2003) *Circulation* 108:2270-2274. Microscopic images were obtained using a Nikon E800 research microscope and digitized with a Nikon DXM1200 camera.

C. Results of Imaging, Histology, Clinical Chemistry and Hematology

All three paramagnetic nanoparticle formulations for use in the experiment (i.e., $a,8_3$-targeted fumagillin nanoparticles, $a,0_3$-targeted nanoparticles without fumagillin and nontargeted fumagillin nanoparticles) were prepared as described in Example 1. All three paramagnetic nanoparticle formulations had similar particle size distributions with nominal diameters ranging from 175 nm to 220 nm and similar paramagnetic payloads (~90,000 gadolinium ions per particle). Both the targeted and non-targeted fumagillin nanoparticles incorporated ~87% of the theoretic drug payload (30 μg fumagillin/ml) for an net payload of ~26 μg/ml. Fumagillin was well retained with less than 9% of the incorporated dosage diffusing from the nanoparticles under sink conditions during in vitro dissolution (FIG. 1). The majority of fumagillin release occurred during the first day (~5%) and further release was undetectable by the fourth day. Generally, the hydrophobic nature of fumagillin permits <10% to be released.

During baseline scanning, $T_1$-weighted black blood images showed no gross evidence of significant plaque development within the wall of the abdominal aorta, i.e., no lumenal narrowing or wall thickening compared to previous experiments utilizing age-matched, nonatherosclerotic rabbits. MRI signal enhancement from the aortic walls of atherosclerotic rabbits injected with $\alpha_v\beta_3$-targeted nanoparticles, both with and without fumagillin, displayed a patchy distribution (FIG. 2, left-hand panels), with generally higher levels of angiogenesis near the diaphragm. Non-targeted nanoparticles (with fumagillin) produced less extensive MRI enhancement of the neovasculature at much lower levels with a similar heterogenous distribution, consistent with results from other studies with non-targeted nanoparticles.

Figure 2:
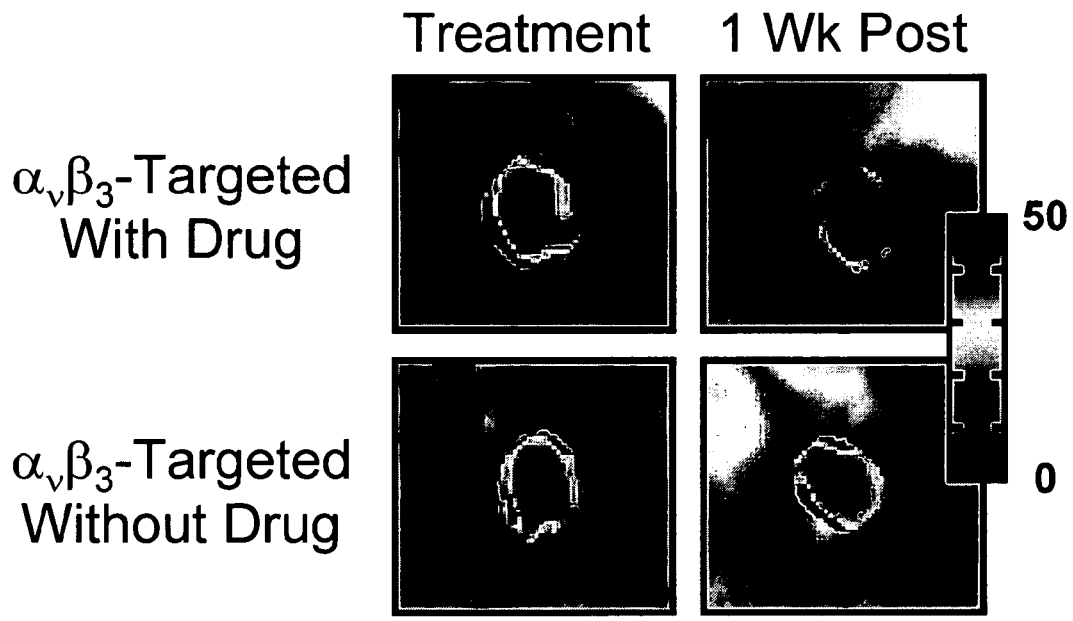
FIG. 2 shows anatomic MR images of abdominal aorta with false-colored overlay of percent signal enhancement at time of treatment (left) and one week post-treatment (right) of atherosclerotic animals injected with $\alpha_v\beta_3$-targeted nanoparticles, either with or without fumagillin. The color-coded signal enhancement is presented in percent above baseline (false-colored from blue to red).
Figure 3:
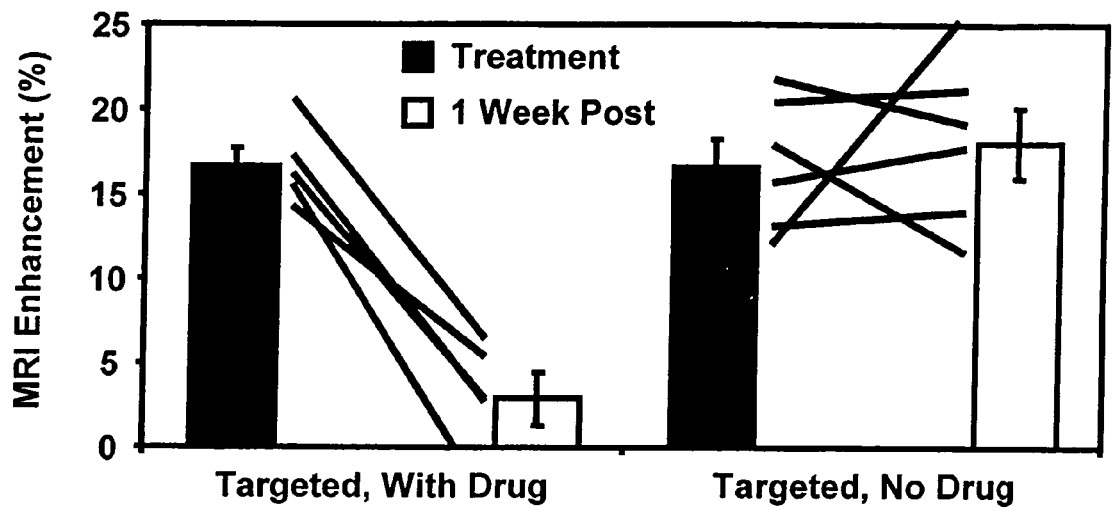
FIG. 3 is a graph which depicts MRI signal enhancement averaged over all imaged sections at the time of treatment (black bars) and one week post treatment (white bars) from aortic walls of atherosclerotic animals injected with targeted nanoparticles, either with or without fumagillin. The solid lines indicate-response of individual animals from time of treatment to one week post treatment.

Similar enhancement was noted at the time of treatment with $\alpha_v\beta_3$-targeted paramagnetic nanoparticles either with (FIG. 2 top) or without fumagillin (FIG. 2 bottom), indicating successful delivery of nanoparticles to the vasa vasorum. MRI signal enhancement averaged over all imaged slices was identical for $\alpha_v\beta_3$-targeted nanoparticles with (16.7±1.1%) and without (16.7±1.6%) fumagillin (FIG. 3, black bars). Non-targeted nanoparticles, however, provided less signal enhancement (10.8±1.1%, p<0.05) compared with either $\alpha_v\beta_3$-targeted formulation, representing nonspecific leakage from the hyperpermeable angiogenic vasculature.

One week after nanoparticle treatment, the residual angiogenic activity within the aortic wall was assessed. Baseline scans were repeated, followed by injection of $\alpha_v\beta_3$-targeted paramagnetic nanoparticles (no drug) and contrast enhancement imaging four hours post-injection. The aortic wall signal intensity at baseline was identical for all groups at the time of treatment and at the one week follow-up, confirming that previously administered paramagnetic nanoparticles were undetectable. This is consistent with the diminished enhancement in the present study at 4 hours compared to previous measurements at two hours (20% vs. 50%, respectively). In fact, minimal enhancement is observed 24 hours post injection, suggesting relatively rapid local metabolism of the nanoparticles.

MRI signal enhancement from angiogenic vasculature one week following $\alpha_v\beta_3$-targeted fumagillin nanoparticle treatment was markedly reduced (2.9±1.6%; p<0.05) in extent (FIG. 2, upper right-hand panel) as well as intensity (FIG. 3), reflecting reduced levels of angiogenesis. By comparison, the MRI signal enhancement one week after treatment with $\alpha_v\beta_3$-targeted nanoparticles lacking fumagillin was undiminished (18.1±2.1%; FIG. 2, lower right-hand panel and FIG. 3). Thus, one week after treatment, a marked reduction in angiogenesis was observed in animals treated with $\alpha_v\beta_3$-targeted nanoparticles with fumagillin versus their no drug counterparts.

Figure 4:
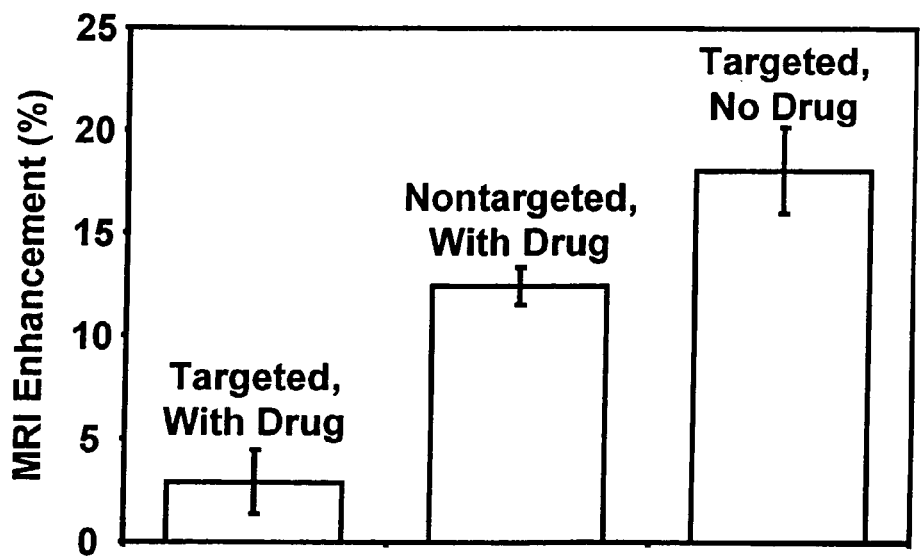
FIG. 4 is a graph which depicts MRI enhancement one week post treatment from aortic walls of atherosclerotic animals injected with targeted nanoparticles, either with or without fumagillin, or with non-targeted particles with fumagillin.

The trends for individual animals (FIG. 3, solid lines) show a highly consistent decrease in all five rabbits treated with $\alpha_v\beta_3$-targeted fumagillin nanoparticles. In stark distinction, MR contrast remained static or increased in five out of the six animals injected with $\alpha_v\beta_3$-targeted nanoparticles lacking fumagillin. $\alpha_v\beta_3$-targeted nanoparticles reveal significantly lower angiogenesis one week after treatment with targeted fumagillin particles (FIG. 4). Treatment with non-targeted fumagillin nanoparticles did not significantly inhibit angiogenesis as determined by MRI signal enhancement one week after treatment (12.4±0.9%) in comparison to $\alpha_v\beta_3$-targeted nanoparticles without fumagillin (FIG. 4).

Figure 5:
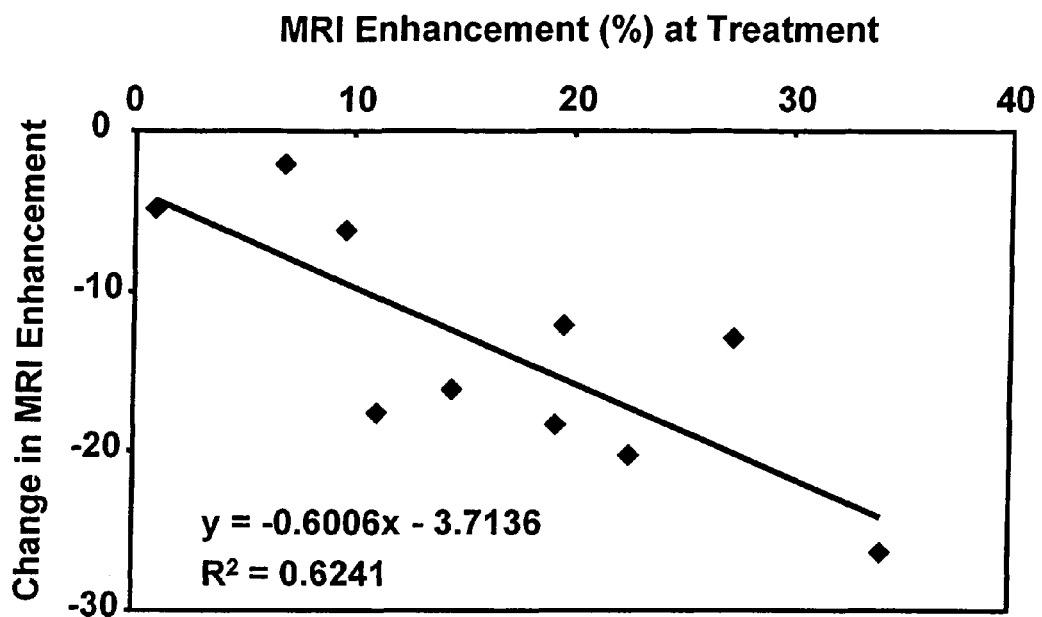
FIG. 5 is a graph which plots the magnitude of MRI enhancement at the time of treatment (horizontal axis) versus the change in MRI enhancement one week after treatment for animals injected with $\alpha_v\beta_3$-targeted nanoparticles with fumagillin.

In the five rabbits treated with $\alpha_v\beta_3$-targeted fumagillin nanoparticles, the aortic enhancement data from each rabbit was subdivided into two broad anatomical locations: diaphragm (top half) and renal arteries (bottom half) and the magnitude of contrast signal detected at the time of treatment was plotted against the percentage of contrast change observed one week post treatment. Aortic areas displaying high MRI enhancement at the time of treatment (i.e., the greatest delivery of drug) had the largest reduction in angiogenesis one week later (FIG. 5). Therefore, imaging provides important feedback for targeted therapies: the adequacy of drug delivery is related to the magnitude of the signal, which in turn correlates with therapeutic effect.

Figure 6:
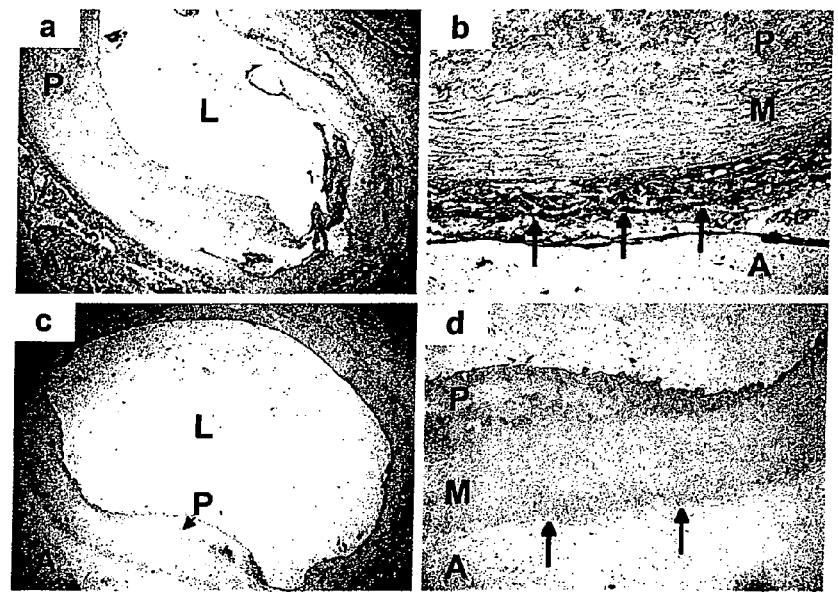
FIGS. 6a-6d depict histological sections of abdominal aorta obtained one week after nanoparticulate treatment. On the images, portions of the aorta are indicated as follows: P —plaque, L—lumen, A—adventitia, M—media.

Examination of abdominal aorta sections obtained one-week after nanoparticulate treatment revealed mild, heterogeneously distributed intimal thickening consistent with early atherosclerosis in all rabbits. Thicker neointimal plaques were generally associated with higher degrees of neovascular proliferation observed along the adventitial—media interface. Although all animals, regardless of treatment group, had intimal plaques heterogeneously interspersed with apparently normal areas, the most prominent intimal pathology was noted in rabbits treated with $\alpha_v\beta_3$-targeted nanoparticles lacking fumagillin (FIG. 6a). In these hyperlipidemic control animals, aortic intimal thickening was associated with underlying angiogenic expansion of the vasa vasorum in virtually all instances (FIG. 6b).

Figure 7:
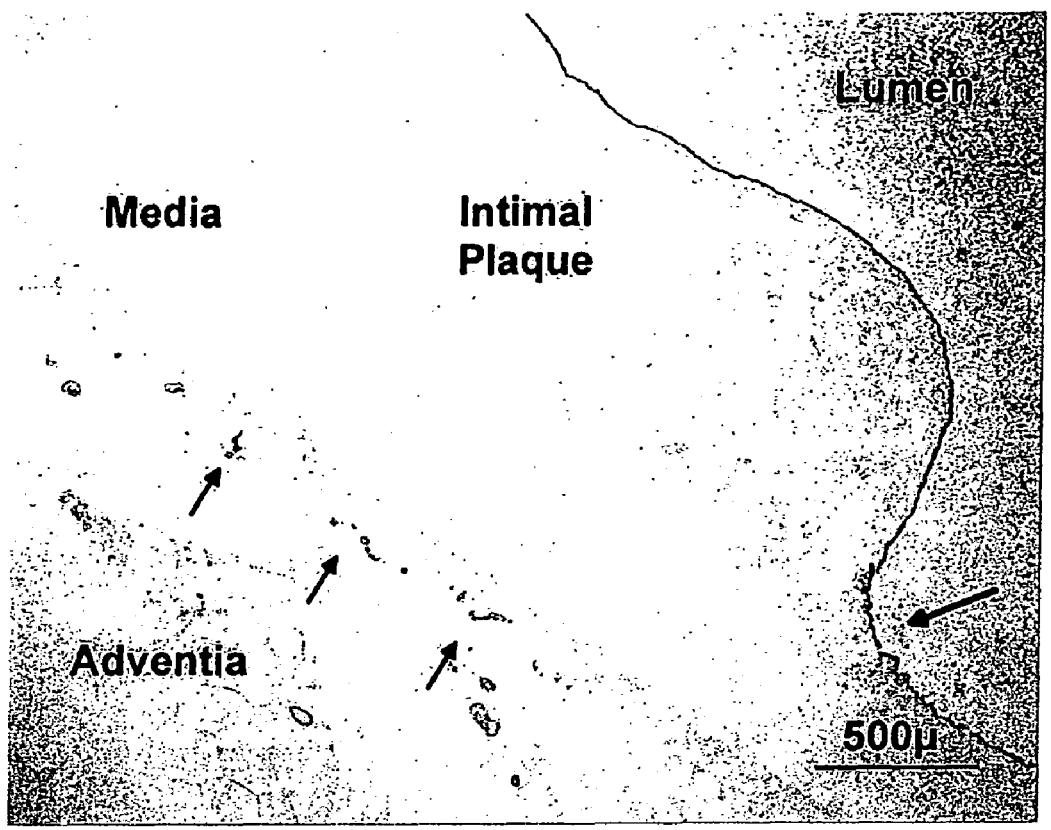
FIG. 7 depicts a histological section of abdominal aorta obtained one week after $\alpha_v\beta_3$-targeted fumagillin nanoparticle treatment. The black arrows indicate a persistent region of angiogenesis in the adventitia associated with plaque and the red arrow indicates an abrupt change in plaque thickness associated with a region where neovascular vasa vasorum expansion is not observed.

In contradistinction, animals given $\alpha_v\beta_3$-targeted fumagillin nanoparticles had sparse intimal plaques with underlying angiogenesis and a majority of plaque without neovascularity. In some sections, intimal plaque was completely circumferential without the expression of $\alpha_v\beta_3$-integrin positive microvasculature, while in others, neovascularity was detected in the adventitia beneath portions of plaque but not below other regions (FIG. 6c). In these instances, plaques were notably thicker above adventitial neovascularity compared to areas without angiogenic vessels (FIG. 6d). Occasionally, persistent regions of angiogenesis in the adventitia were associated with plaque, which abruptly changed thickness in regions where neovascular vasa vasorum expansion was not observed (FIG. 7).

Histology from rabbits treated with nontargeted fumagillin nanoparticles was generally similar to aortic sections exposed to the control $\alpha_v\beta_3$-targeted nanoparticles without fumagillin. Although some plaques showed little or no angiogenesis (similar to animals receiving $\alpha_v\beta_3$-targeted nanoparticles with fumagillin), the frequency of these observations was less common.

Baseline serum cholesterol levels were 1565±155 mg/dl. After nanoparticle treatment, all rabbits were fed normal rabbit chow, but total serum cholesterol levels remained elevated and were similar for all three groups at the time of sacrifice ($\alpha_v\beta_3$-targeted fumagillin nanoparticles: 1132±192 mg/dl; $\alpha_v\beta_3$-targeted control nanoparticles: 1454±221 mg/dl; nontargeted fumagillin nanoparticles: 1485±213 mg/dl). One week after treatment, no nanoparticle formulation ($\alpha_v\beta_3$-targeted or nontargeted, with or without fumagillin) altered electrolytes, hepatic function, or hematology compared to published normal ranges (see, for example, Olfert et al. (1993) *Guide to The Care and Use of Experimental Animals*. 2 ed. Ontario, Canada: Canadian Council on Animal Care).

As noted above, Moulton et al. (1999) described a reduction in intimal vessels and diminished atheroma expansion with administration of 30 mg TNP-470 (a fumagillin analogue) per kg every other day for 13 weeks, or a total of 1.67 g/kg. The results shown above with targeted nanoparticles was achieved with a single administration of 30 μg/kg of fumagillin. Thus, the use of the targeted nanoparticles to deliver the fumagillin allowed for a $5.6\times10^4$ fold lower amount of the drug to be administered as compared to the amount of TNP-470 administered in Moulton et al. (1999).

EXAMPLE 2

Targeted Atherosclerosis Treatment—Secondary Prevention Strategy

The following model will be used to determine the effect of suppressing neovascular development in normal and atherosclerotic arteries following balloon-overstretch injury with $\alpha_v\beta_3$-targeted fumagillin paramagnetic nanoparticle on neointimal development.

Normal and cholesterol fed New Zealand White rabbits (~90 days on 0.25% cholesterol diet) will undergo baseline abdominal aortic MR imaging (proton and 19fluorine) followed by intravenous injection of paramagnetic nanoparticles targeted to $\alpha_v\beta_3$-integrin (e.g., as described in Example 1 without the therapeutic agent). Two hours post-injection, animals will be re-imaged following similar procedures to obtain pre-injury MRI signals.

Animals will be catheterized and balloon-overstretch injured in the abdominal aorta. All animals will continue on their pre-study diets. On days 0, 5, 10 and 15 post injury, angiogenesis development in the injured vascular segment will be assessed by re-imaging with paramagnetic nanoparticles (as before the injury) and compared to pre-injury signal levels. MRI angiograms will be performed in all animals prior to molecular imaging to assess in vivo lumen caliber. After MR imaging on day 15, each animal will be necropsied and the injured aortic segment removed for histology (e.g., H&E, $\alpha_v\beta_3$-integrin, rabbit endothelial markers, macrophages). This assessment will provide temporal information regarding post-injury angiogenesis for comparison to the study of the same in the presence of $\alpha_v\beta_3$-targeted fumagillin nanoparticles.

For the study with the targeted nanoparticles containing a therapeutic agent, normal and cholesterol fed New Zealand White rabbits (~90 days on 0.25% cholesterol diet) will undergo will balloon-overstretch injury in the abdominal aorta which will be followed baseline abdominal aortic MRI imaging (proton and 19 fluorine) with paramagnetic nanoparticles targeted to $\alpha_v\beta_3$-integrin. MRI (TOF, no added contrast) angiograms will be performed in all animals prior to molecular imaging to assess in vivo lumen caliber. On the designated day (as determined in above study) half of the animals in each dietary regimen will receive paramagnetic nanoparticles with fumagillin targeted to $\alpha_v\beta_3$-integrin (as described in Example 1) and the remainder will be given the molecular imaging agent without drug. Two hours post-injection, animals will be re-imaged following similar MR procedures. All animals will continue on their pre-study diets. Angiogenesis progression and neointimal stenosis in the injured vascular segment will be assessed 14 and 28 days later by re-imaging with $\alpha_v\beta_3$-targeted paramagnetic nanoparticles after performing an MR angiogram of the vascular segment. After MR imaging on day 28, each animal will be necropsied and the injured aortic segment removed for histology (e.g., H&E, $\alpha_v\beta_3$-integrin, rabbit endothelial markers, macrophages).

What is claimed is:

1. A method for inhibiting atherosclerotic plaques in a subject which method comprises administering to a subject diagnosed with atherosclerosis, a composition comprising a nanoparticulate carrier contained in an emulsion and an $\alpha_v\beta_3$ targeting ligand and an anti-angiogenic agent, wherein the targeting ligand and anti-angiogenic agent are coupled through colocalization in said nanoparticles; and wherein the anti-angiogenic agent is fumagillin, TNP470 or rapamycin, wherein said anti-angiogenic agent is effective at a dosage at least 56,000 fold lower than that required when said anti-angiogenic agent is administered as a free drug.

2. The method of claim 1, wherein the nanoparticulate carrier is a high boiling liquid fluorocarbon coated with lipid/surfactant.

3. The method of claim 1, wherein the administering is systemic.

4. The method of claim 3, wherein the administering is intravenous.

5. The method of claim 1, wherein the targeted carrier further comprises an image contrast agent, and the method further comprises imaging the targeted carrier after administration to the subject.

6. The method of claim 1, wherein said composition is administered to said subject one, two or three times.

* * * * *